US005709843A

United States Patent [19]

Reisner

[11] Patent Number: 5,709,843

[45] Date of Patent: Jan. 20, 1998

[54] ENGRAFTMENT AND DEVELOPMENT OF XENOGENEIC CELLS IN NORMAL MAMMALS HAVING RECONSTITUTED HEMATOPOIETIC DEFICIENT IMMUNE SYSTEMS

[75] Inventor: Yair Reisner, Tel Aviv, Israel

[73] Assignee: Yeda Research and Development Co. Ltd., Rehovot, Israel

[21] Appl. No.: 347,088

[22] Filed: Nov. 23, 1994

Related U.S. Application Data

[60] Division of Ser. No. 61,706, May 17, 1993, which is a continuation-in-part of Ser. No. 892,911, Jun. 3, 1992, abandoned, and Ser. No. 792,480, Nov. 15, 1991, abandoned, said Ser. No. 892,911, is a continuation-in-part of Ser. No. 792,480, which is a continuation-in-part of Ser. No. 618,303, Nov. 26, 1990, abandoned.

[30] Foreign Application Priority Data

Jan. 15, 1990 [IL] Israel .......... 93067
Jun. 4, 1991 [IL] Israel .......... 98 369

[51] Int. Cl.$^6$ .......... A61K 49/00; G01N 31/00; A01N 63/00; A01N 65/00

[52] U.S. Cl. .......... 424/9.2; 424/9.1; 424/93.1; 424/93.3; 424/93.7; 424/93.71; 424/520; 435/4; 435/5; 800/2

[58] Field of Search .......... 800/2; 424/9.2, 424/9.1, 93.1, 93.3, 93.7, 93.71, 520; 435/5, 4

[56] References Cited

U.S. PATENT DOCUMENTS

| | | | |
|---|---|---|---|
| 4,683,200 | 7/1987 | Hirohashi et al. | 435/70.21 |
| 5,147,784 | 9/1992 | Peault | 435/7.24 |

FOREIGN PATENT DOCUMENTS

| | | |
|---|---|---|
| 0322240 | 12/1988 | European Pat. Off. . |
| 0469632 | 2/1991 | European Pat. Off. . |
| 8912823 | 12/1989 | WIPO . |
| 9116451 | 10/1991 | WIPO . |
| 9116910 | 11/1991 | WIPO . |
| 9118615 | 12/1991 | WIPO . |
| 9203918 | 3/1992 | WIPO . |
| 9206715 | 4/1992 | WIPO . |

OTHER PUBLICATIONS

Lubin, I. et al., "Engraftment and Development of Human T and B Cells in Mice After Bone Marrow Transplantation", Reports, Apr. 19, 1992, pp. 427–431.

Murphy, W. et al., "An Absence of T Cells in Murine Bone Marrow Allografts Leads to an Increased Susceptibility to Rejection by Natural Killer Cells and T Cells", *Journal of Immunology 144*:3305–11 (1990).

McCune, J.M. et al., "The SCID–hu Mouse: Murine Model for the Analysis of Human Hematolymphoid Differentiation and Function", *Science 241*:1632 (1988).

Sykes, M. et al., "Mixed Allogeneic Chimerism as an Approach to Transplantation Tolerance", *Immunology Today 9(1)*:23–27 (1988).

Bosma, G.C., et al., "A Severe Combined Immunodeficiency Mutation in the Mouse", *Nature 301*:527 (1983).

(List continued on next page.)

*Primary Examiner*—Brian R. Stanton
*Attorney, Agent, or Firm*—Browdy and Neimark

[57] ABSTRACT

Non-human chimeric mammals are created from a mammal having hematopoietic cells replaced with hematopoietic cells from a hematopoietic deficient mammal donor, and optionally in which xenogeneic cells and/or tissue are engrafted. The xenogeneic, preferably human, cells or tissue may be hematopoietic cells, in which case the chimeric mammal can produce xenogeneic B and/or T cells, and can be used as a source of mammalian, preferably human, monoclonal antibodies and/or T cells. Alternatively, the xenogeneic cells or tissue may be non-hematopoietic, such as normal or pathological cells or tissue, which can form a stable transplant in the chimeric mammal and thus can be used as an animal model of various pathologies or to test therapeutic or diagnostic agents or modalities.

23 Claims, 13 Drawing Sheets

OTHER PUBLICATIONS

Nakamura, T. et al., "Successful Liver Allografts in Mice by Combination with Allogeneic Bone Marrow Transplantation", *Proc. Natl. Acad. Sci. USA 83*:4529 (1986).

Kamel-Reid, S. et al., "A Model Human Acute Lymphoblastic Leukemia in Immune-Deficient SCID Mice", *Science* 246:1597 (1989).

Kamel-Reid, S. et al., "Engraftment of Immune-Deficient Mice with Human Hematopoietic Stem Cells", *Science 242*:1706 (1989).

McCune, J.M. et al., "Pseudotypes in HIV-Infected Mice", *Science 250*:1152–1154 (1990).

Miyama-Inaba, M. et al., "Isolation of murine pluripotent hemopoietic stem cells in the Go phase", *Biochemical and Biophysical Research Communications, 147(2)*:687–695 (1987).

Mosier, D.E. et al., "Transfer of a functional human immune system to mice with severe combined immunodeficiency", *Nature 225*:256–259 (1988).

Namikawa, R. et al., "Infection of the SCID-hu Mouse by HIV-1", *Science 242*:1684–1686 (1988).

Namikawa, R. et al., "Long-Term Human Hematopoiesis in the SCID-hu Mouse", *J. Exp. Med. 172*:1055–1063 (1990).

Reisner, Y. et al., "Transplantation for Severe Combined Immunodeficiency With HLA-A,B,D,DR Incompatible Parental Marrow Cells Fractioned by Soybean Agglutinin and Sheep Red Blood Cells", *Blood 61*:341 (1983).

Keever, C.A. et al. "Immune Reconstitution Following Bone Marrow Transplantation: Comparison of Recipients of T-Cell Depleted Marrow With Recipients of Conventional Marrow Grafts", *Blood 73*:1340 (1989).

Schuler, W. et al., "Rearrangement of Antigen Receptor Genes Is Defective in Mice with Severe Combined Immune Deficiency", *Cell 46*:963–972 (1986).

Reisner, Y. et al., "Transplantation for Acute Leukaemia with HLA-A and B Nonidentical Parental Marrow Cells Fractioned with Soybean Agglutinsin and Sheep Red Blood Cells", *Lancet ii*:327 (1987).

Barry et al., "Successful Engraftment of Human Postnatal Thymus in Severe Combined Immune Deficient (SCID) Mice: Differential Engraftment of Thymic Components With Irradiation Versis Anti-asialo GM-1 Immuno-Suppressive Regimens", *J. Exp. Med.* 173:167–180 (1991).

Kamel-Reid, et al., "A Model of Human Acute Lymphoblastic Leukemia in Immune-Deficient SCID Mice", *Reports,* 22:1597–1600 (1989).

Van Bekkum, D.W., et al., *Bone Marrow Transplantation: Biological Mechanisms and Clinical Practice,* Dekker, New York, pp. 311–350.

Giovanella et al, "Heterotransplantation of Human Cancers into Nude Mice", *Cancer* 42:2269–2281 (1978).

ENGRAFTMENT AND DEVELOPMENT OF XENOGENEIC CELLS IN NORMAL MAMMALS HAVING RECONSTITUTED HEMATOPOIETIC DEFICIENT IMMUNE SYSTEMS

CROSS REFERENCE TO RELATED APPLICATIONS

The present application is a division of application Ser. No. 08/061,706, filed May 17, 1993, which is a continuation-in-part of each of application Ser. No. 07/892,911, filed Jun. 3, 1992 now abandoned, and application Ser. No. 07/792,480, filed Nov. 15, 1991 now abandoned, the entire contents of each of which applications are hereby incorporated entirely herein by reference. Application Ser. No. 07/892,911, filed Jun. 3, 1992, now abandoned is a continuation-in-part of application Ser. No. 07/792,480, filed Nov. 15, 1991 now abandoned, which is a continuation-in-part of application Ser. No. 07/618,303, filed Nov. 26, 1990, now abandoned, the entire contents of which is also hereby incorporated by reference.

BACKGROUND OF THE INVENTION

1. Field of the Invention

The present invention relates to non-human chimeric mammals created by replacement of hematopoietic cells from a hematopoietic deficient donor meal, optionally in which additional replacement with xenogeneic cells and/or tissue are engrafted, as well as to methods for the production and use of such mammals as animal models of human diseases and as a source of human monoclonal antibodies and cytotoxic T cells.

2. Description of the Background Art

Transplantation of human hematopoietic tissues and cells has been attempted in immune-deficient animals. Partial myeloid engraftment in the immune-deficient Bg/Nu/Xid (BNX) mouse following human bone marrow transplantation (Kamel-Reid et al (1988) *Science* 242:1706) and partial lymphoid engraftment following grafting of fetal liver together with fetal thymus under the kidney capsule (McCune et al (1988) *Science* 241:1632; EP publication No. 322,240) or peripheral blood lymphocytes (Mosier et al (1988) *Nature* 335:256) were achieved in the severe combined immunodeficient (SCID) mouse. In particular, it has been shown that engrafted human lymphocytes can produce antibodies to a recall antigen (Mosier (1991) *Advances in Immunology* 50:303) and that they can be infected with HIV (Namikawa et al (1990) *J. Exp. Med.* 172:1055; Mosier et al (1991) *Science* 251:791). While investigating the SCID mouse as a model for lymphocyte differentiation and regulation, Bosma et al (1983) *Nature* 301:527–530) transplanted sublethally irradiated (550 rad) BALB/c mice with SCID mouse bone marrow cells, but without success. None of the BALB/c mice showed SCID allotype. Also, it has been demonstrated that more relevant models for autoimmunity could be established in SCID mice (Lupus; *Myasthenia gravis*).

Although all these important applications were demonstrated, it also became apparent that the engrafted human T cells in the SCID mouse are in functional anergy and that most of their immune functions are lost, such as the ability to generate cytotoxic T lymphocytes against viral antigens or a primary antibody response. This anergy could be explained by, the marked genetic disparity, which could lead to poor crossreactivity between human and mouse cytokines, homing receptors and especially the histocompatibility antigens which dominate the immune response. One potential approach which might partially overcome some of these barriers could be the use of transgenic mice carrying the appropriate human transgene, such as human HLA Class I or Class II, or human cytokines. Alternatively, the functional anergy of human T cells could be avoided if it were possible to engraft other rodents, which may present different crossreactivities, with human immune response molecules. However, such animals are, in most instances, not immunedeficient, and it is therefore important to develop a general approach for the transplantation of human hematopoietic tissues in normal rodents.

Following heavy suppression of the immune and hematopoietic systems, as with lethal total body irradiation (TBI), mice typically die within 2 weeks if additional bone marrow is not provided. Even if human stem cells could theoretically grow in such mice and reconstitute the mouse's hematopoietic system, it would be expected that their slow rate of differentiation into mature immunocompetent lymphocytes or other leukocytes would prevent them from reaching large enough numbers to protect the mice from infections. Furthermore, inadequate replenishing of hematopoietic compartments would not protect the mice from death by hematopoietic failure. On the other hand, sublethal conditioning protocols (e.g., sublethal TBI), which spare substantial numbers of hematopoietic and lymphoid cells, would enable endogenous murine cells to compete effectively with transplanted human cells, and ultimately reject the human graft.

Nakamura, T. et al. (1986) *Proc. Natl. Acad. Sci. USA* 83:4529–4532, described successful liver allografts established by combination with allogeneic bone marrow transplantation. Thus, liver pieces from a BALB/c mouse were accepted when transplanted under the kidney capsules of lethally irradiated C3H/H3N mice which were reconstituted with bone marrow of BALB/c mice. However, such chimeric mice were found not to be useful with transplanted hematopoietic cells without the same allotype as the transplanted liver cells, since liver pieces from C57BL/6J mouse (differing in their H-2 from the bone marrow donor) were rejected. Therefore, in this system, tolerance towards liver engrafting is confined to the strain of the bone marrow donor. It would be desirable to engraft tissue or cells from donors other than the bone marrow donor's or the recipient's endogenous bone marrow, including human xenografts, in a non-human mammal. This, however, has not been previously achieved.

The use of T cell depleted allogeneic bone marrow grafts has been found to increase the rejection of such transplants by natural killer cells and T cells. Murphy et al. (1990) *J. Immunol.* 144:3305–3310 disclose that the use of T cell deficient SCID mice as bone marrow cell donors for an allogeneic transplant into mice having destroyed bone marrow, resulted in markedly enhanced rejection compared to syngeneic control grafts. Accordingly, this reference teaches away from the use of immunodeficient mice as bone marrow donors to allogeneic or xenogeneic recipients having a destroyed immune system.

The use of PBL as a source of human hematopoietic cells was found to be unsuccessful in lethally irradiated mice which have natural antibodies in their serum. Only strains which were incapable of making such antibodies, due to immune deficiencies or to post-natal treatment with anti-mouse IgM, were engrafted but developed graft-versus-host disease (Huttes et al (1992) *Eur. J. Immunol.* 91(1):197). Accordingly, this reference teaches away from the use of human hematopoietic cells for transplantation in normal lethally irradiated rodents.

PCT publication no. WO 91/16910, published (Nov. 14, 1991), by Mayo et al. and assigned to SyStemix, Inc., discloses human monoclonal antibody production in mice. Human fetal lymphoid tissue is implanted in mice followed by stimulation with an immunogen, harvesting and cloning. The human fetal lymphoid tissue must be implanted into an immunocompromised mammal at a site where the tissue becomes vascularized and connected to lymphoid tissue and the cells proliferate, followed by applying a stimulus to the tissue, and determining the effect of the stimulus on the response of the cells. The stimulus can be immunization with an immunogen or contact with a drug.

EP 469,632, published Feb. 5, 1992, by McCune et al. and assigned to SyStemix, Inc., discloses administration of a stimulus, able to induce a physiological response from tissue cells of a particular species, to an immunocompromised host, other than a primate, lacking at least functional T cells but including tissue cells of the species; and determining the effect of the stimulus. The tissue cells are vascularized, non-transformed solid organ tissue. Also SCID/hu mice are disclosed which are infected in the human tissue with a pathogen tropic for this tissue, wherein the solid tissue is a hematopoietic tissue, and the host is a SCID/SCID mouse. Such host can be used to evaluate the effect of drugs and vaccines, and of agents for conditions on specific tissue or the immune system. The human tissue is disclosed to remain viable for more than four weeks.

PCT publication no. WO 91/16451, published Oct. 31, 1991, by Peault and assigned to SyStemix, Inc., discloses a method for affecting the ability of human cells to produce T-lymphocytes and of progenitor cells to self-regenerate, by implanting human thymus tissue which has been depleted of lymphoid cells into an immunocompromised non-human mammal at a site where it becomes vascularized and assaying for the presence of T-lymphocytes having the desired HLA composition. The host is a SCID/SCID mouse and the thymus is fetal tissue. The cellular composition is concentrated for CD34+ cells and is implanted in the kidney capsule.

PCT publication No. WO 89/12823, published (Dec. 28, 1989) by Mosier et al and assigned to Medical Biology Institute, discloses the use of SCID mice as recipients for human immune cells or tumor cells to act as an animal model for human HIV, tumor or human immune responses. Other immunodeficient hosts are suggested, such as nude mice.

PCT publication No. WO 91/18615, published (Dec. 12, 1991), by Baum et al and assigned SyStemix, Inc., discloses the production of human peripheral blood cells in xenogeneic immunocompromised non-human mammal hosts. After introduction of human fetal bone marrow into a mammalian host, after irradiation of the host, for example, a SCID/SCID mice at 200–400 RADs as whole body or a single dose of 600 RADs after shielding of thorax and abdomen. Non-human mammals having human peripheral blood cells present as at least 2%, 5% or 15% of the total peripheral blood cells is taught.

Citation of documents herein is not intended as an admission that any of the documents cited herein is pertinent prior art, or an admission that the cited documents is considered material to the patentability of the claims of the present application. All statements as to the date or representation as to the contents of these documents is based on the information available to the applicant and does not constitute any admission as to the correctness of the dates or contents of these documents.

SUMMARY OF THE INVENTION

It is an object of the present invention to overcome one or more deficiencies of the related art.

It is a further object of the present invention to provide chimeric non-human mammals having xenogeneic hematopoietic cells, which mammals may be used to produce commercially useful amounts of human monoclonal antibodies or T cells, or which can be used to provide superior models of human or mammalian diseases, including controls, compared to known animal models.

It is another object of the present invention to provide chimeric non-human mammals having stable xenogeneic non-hematopoietic cells. Such chimeric mammals of the present invention have xenogeneic, such as human, pathological and/or normal cells or tissue, derived from humans or domestic animals.

It is yet a further object of the present invention to provide methods for the production of such chimeric non-human mammals in order to permit the engraftment of xenogeneic cells or tissue.

It is still another object of the present invention to provide methods for production of xenogeneic antibodies or T cells, and particularly human monoclonal antibodies and cytotoxic T cells, using chimeric mammals of the present invention.

Further objects of the present invention are to provide methods of using the chimeric mammals of the present invention to test potential drugs and therapy for diseases of humans or other higher mammals in a mouse or other laboratory animal having the xenogeneic cells or tissue of the mammal in which the drug or therapy is intended to be used.

These and other objects of the present invention will become apparent after full consideration of the figures and detailed description of the present invention.

The present invention is thus directed, in one aspect, to a non-human chimeric mammal M4 having xenogeneic cells or tissue, preferably with long term stability, the mammal M4 comprising a mammal M1, the hematopoietic cells of which have been substantially destroyed, the mammal M1 having transplanted therein cells from at least two different sources, at least one of the sources being hematopoietic cells derived from a mammal M2 having a hematopoietic deficiency, and at least one second of the sources being xenogeneic cells or tissue derived from a mammal M3 of a species other than that of mammals M1 and M2. Preferably mammals M1 and M2 are both mice, or M1 is a rat and M2 is a mouse, and mammal M3 is human. The hematopoietic deficiency of mammal M2 may be genetically or non-genetically determinable.

The xenogeneic cells or tissue derived from the mammal M3 may be hematopoietic cells which, together with the hematopoietic cells derived from the mammal M2, serve to replace the hematopoietic cells of the mammal M1 which had been substantially destroyed.

Alternatively, the xenogeneic cells or tissue may be non-hematopoietic cells, such as pieces of normal or pathological cells or tissue, e.g., the non-limiting examples of organ tissue or malignant cells or tissue.

The mammals M1, after having their hematopoietic cells substantially destroyed and after being transplanted with the hematopoietic cells of an hematopoietic deficient mammal M2, have the same hematopoietic deficiency as the hematopoietic deficient donor mammal M2, as their hematopoietic cells have been replaced by the hematopoietic cells of such donor mammal M2. Because of the hematopoietic deficiencies in such M1–M2 chimeric host mammal, however, xenogeneic cells or tissue derived from mammal M3 are not rejected. Instead of being a normal mammal, the host mammal M1 may be a nude mammal or transgenic mammal in order to supply other predetermined characteristics for improving its use as an animal model of human or other mammalian diseases.

Another aspect of the present invention is a M1–M2 mammal which is obtained when a normal, nude or transgenic mammal M1 has had its hematopoietic cells substantially destroyed and replaced by hematopoietic cells derived from a mammal M2 having a hematopoietic deficiency. Such mammals, preferably mice, rats or other laboratory animals, are useful as intermediates for the production of non-human chimetic mammals M4 of the present invention having xenogeneic cells or tissue derived from a mammal M3.

According to another aspect of the present invention, a method is provided for the production of the chimeric mammal M4, as described above, having xenogeneic cells or tissue derived from a mammal M3 and also having hematopoietic cells derived from a mammal M2 having a hematopoietic deficiency, the method comprising (a) treating a non-human mammal M1 so as to substantially destroy the hematopoietic cells thereof; and (b) transplanting said treated mammal M1 with (1) xenogeneic cells or tissue derived from a mammal M3 of a species other than that of mammal M1; and with (2) hematopoietic cells derived from a mammal M2, of a species other than that of M3, having a genetically determinable or non-genetically determinable hematopoietic deficiency.

In one preferred embodiment of the method of the present invention, the xenogeneic cells or tissue derived from a mammal M3 are hematopoietic cells. In this embodiment, the non-human mammal M1 is subjected to a treatment to substantially destroy its hematopoietic cells. Thereafter, the treated mammal M1 is transplanted with (1) hematopoietic cells originating from a mammal M3 of a species other than that of mammal M1, and (2) hematopoietic cells originating from a mammal M2, of a species other than that of M3, having a hematopoietic deficiency, preferably a genetic deficiency. In this manner, a chimeric non-human mammal M4 is created having hematopoietic cells derived from mammal donor M2 and further having one or more hematopoietic cell lineages from mammal donor M3, the hematopoietic cell lineages from mammal M3 corresponding to at least one cell lineage lacking from mammal M2 due to said hematopoietic deficiency.

In the most preferred embodiment of the present invention, the non-human recipient mammal, M1, is a rodent or other mammal commonly used as a laboratory animal, preferably a mouse or rat, the non-human mammal donor, M2, is a SCID mammal, and the mammal donor M3 is a human or another mammal for which cures to veterinary diseases are being sought, such as ovine, bovine and equine, canine or feline animals.

In another preferred embodiment of the method of the present invention, the xenogeneic cells or tissue derived from a mammal M3 are non-hematopoietic cells. In this embodiment, the non-human mammal M1 is treated in the same way to substantially destroy its hematopoietic cells. Thereafter, the treated mammal M1 is transplanted with hematopoietic cells originating from a mammal M2 having a hematopoietic deficiency, preferably a genetic hematopoietic deficiency, as well as with tissue or cells other than normal hematopoietic cells originating from a mammal M3. In this manner, a chimeric non-human mammal M4 is obtained having hematopoietic cells derived from mammal donor M2 and further having tissue or cells, other than normal hematopoietic cells, from mammal donor M3. In a preferred embodiment of this method, the xenogeneic cells or tissue derived from mammal donor M3 are human solid tumors, leukemias or other malignant tissue or cells. In another preferred embodiment, the xenogeneic cells or tissue comprise normal or pathological cells or tissue derived from human organs.

Another aspect of the present invention is a method for providing mammalian, preferably human, monoclonal antibodies specific for an antigen, by immunizing a chimeric non-human mammal M4 according to the present invention, in which the xenogeneic cells from mammal donor M3 are hematopoietic cells, with an antigen such that xenogeneic antibody-producing cells are produced in the chimeric mammal. The antibody-producing cells are then removed and immortalized, followed by screening for the presence of the desired antibody. After the desired antibody-producing cells are selected, they are cloned and the antibodies produced by such selected, cloned, immortalized antibody producing cells are isolated therefrom.

The antigen is administered by immunizing with any suitable antigenic determinant, such as proteins, pathological cells, tissue or extracts thereof presenting a pathology-related antigen capable of eliciting antibodies from the antibody-producing cells. The obtained antibodies specific for the pathology-related antigen may be administered to the mammal from which the pathological cells, tissue or other material were derived, in a therapeutically effective amount, such that the antibody is effective in treating the pathology in that mammal. Examples of such pathological cells, tissue or other material are those associated with a malignancy, cancer or viral infection, preferably in a human. Diagnostic methods are also provided according to the present invention using such human monoclonal antibodies.

The present invention is also directed to monoclonal antibodies or portions thereof, antibody-producing cells and cell lines producing said monoclonal antibodies, said cell lines being provided according to methods of the present invention, or by genetic or protein engineering of the nucleic acid encoding the antibodies or peptide portions of such antibodies. It is also directed to hybridomas or other antibody-producing cell lines.

The present invention also relates to a method for evaluating the efficacy of a therapeutic agent or modality potentially useful for treating a human disease. In this embodiment, a chimeric mammal M4 according to the present invention is infected with a pathogen which causes the human disease being studied. The mammal M4 is one in which the xenogeneic cells or tissue derived from mammal M3 are normal human cells or tissue which become infected by said pathogen when infecting a human. The therapeutic agent or modality to be tested is then administered to the infected chimeric mammal M4 and it is tested for the presence or amount of the pathogen or a pathogenic antigen thereof in a body fluid or tissue of the infected chimeric mammal. The efficacy of the agent or modality is inversely related to the amount or presence of said pathogen or antigen, thereby evaluating the efficacy of the agent.

In a further aspect of the present invention, the mammal M4 is obtained by transplantation with cells originating from pathological cells and/or tissue of a mammal M3 and the therapeutic activity of at least one therapeutic agent or combination of agents or modalities may be evaluated in the transplanted chimeric mammal M4 as a model of the pathology in mammal M3, such as where M3 is a human. Furthermore, when the xenogeneic cells or tissue from mammal M3 are pathological cells and/or tissue of a specific human patient, the therapeutic activity of a proposed therapeutic treatment may be evaluated in the transplanted chimeric mammal M4 as a model of the pathology of that patient.

In another aspect of the present invention, human or other mammalian T-cells, such as the non-limiting example of cytotoxic T lymphocytes (CTL), against a pathogenic antigen can be provided for use in therapeutic or diagnostic applications. In this method, a chimeric non-human mammal M4 having xenogeneic CTL precursor cells derived from a mammal M3 is immunized with suitable antigen capable of eliciting cytotoxic T cells in recoverable amounts in the mammal M4. Such antigens are preferably derived from the subject which is eventually to be treated with the elicited CTLs. The CTLs may then be recovered from the immunized mammal M4. The recovered CTLs are capable of providing a therapeutic effect against the pathology by lysing the pathological cells or tissue upon administration to a patient suffering from such a pathology. Preferably, the pathological cells and the CTL precursor cells are from the same human or meal.

According to another method of the present invention, the treatment of a human or other mammal suffering from a pathology is provided by administering a therapeutically effective amount of the above CTLs, such that the pathological cells or tissue in a mammal to which the CTLs are administered, are bound and lysed by the CTLs. Preferably the pathological cells are cancer or virally infected cells.

Methods for treating mammal pathologies are also provided by administering to such a mammal having such a pathology, a therapeutically effective amount of the mammal monoclonal antibody, or portion thereof, specific for the pathology-related antigen, such that the antibody is effective in treating the pathology in the mammal. Preferably the mammal is human.

Diagnostic methods are also provided according to the present invention using such human monoclonal antibodies.

Other features, advantages, embodiments, aspects and objects of the present invention will be clear to those skilled in the areas of relevant art, based on the description, teaching and guidance presented herein.

DESCRIPTION OF THE FIGURES

FIG. 2A: Spleen cells from a control mouse transplanted with SCID bone marrow alone. FIG. 2B: Normal human PBL. FIG. 2C: Spleen cells of human-mouse chimera (No. 2 of the first series, 9 months post-transplant) Cells (25×10$^3$/well) were cultured for 7 days in RPMI medium containing fetal calf serum (10%) and IL-2 (20 μg/well).

(FIG. 8E).

DETAILED DESCRIPTION OF TEE PREFERRED EMBODIMENTS

Figure 1:
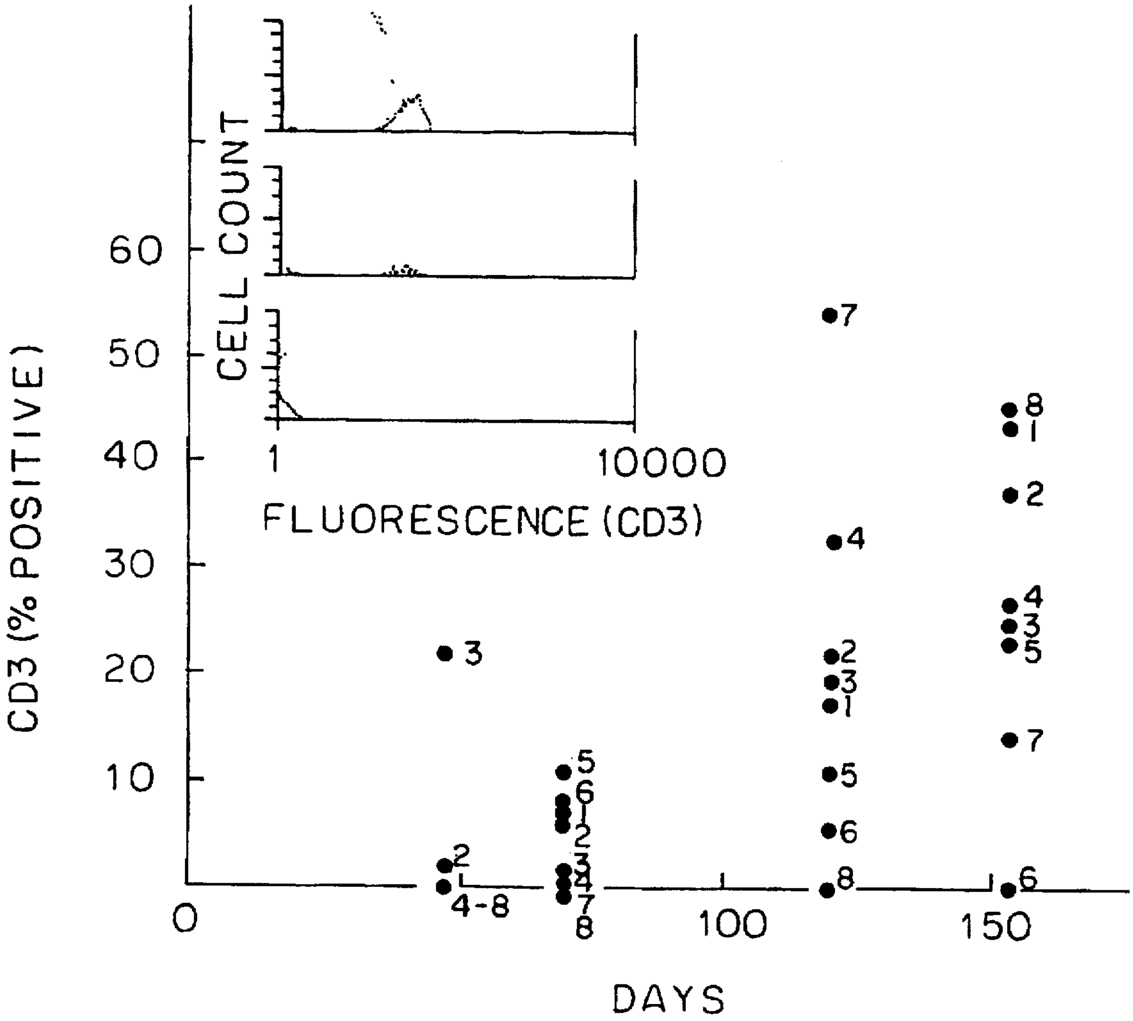
FIG. 1 is a graphical representation showing the development of human CD3$^+$ cells in the peripheral blood of BALB/c mice transplanted with human and SCID mouse bone marrow. Human CD3$^+$ cells were analyzed by cytofluorimetry with anti-CD3 (Leu4). Numbers 1–7 which identify the data points refer to surviving mice of the first series of experiments (see Table 1). The inset shows results of a typical experiment carried out on day 49 post-transplant. Staining of normal human peripheral blood lymphocytes (PBL) with anti-CD3 (upper section) is compared to staining of PBL from mouse No. 3 (middle section) and from a control mouse (lower section) transplanted with SCID bone marrow alone. Staining of normal mouse PBL was identical to that found for the control mouse.

In an preferred embodiment, the present invention relates generally to the production and use of non-human chimeric M4 mammals derived from M1 mammals having their natural hematopoietic cells replaced with syngeneic, allogeneic or xenogeneic hematopoietic cells from hematopoietic deficient M2 mammal donors, and in which such M1–M2 meals have xenogeneic cells and/or tissue from an unrelated mammal M3 engrafted, thereby producing the M4 chimeric meals. Such chimeric animals of the present invention can provide models of various human or domestic animal pathologies, as well as sources of human or other mammalian monoclonal antibodies and/or T cells reactive to specific antigens, which antibiotics and/or T cells are capable of being used as therapeutic and/or diagnostic agents for the treatment and/or diagnosis of human or other mammalian diseases. The mammal M3 xenogeneic cells or tissue may be at least one of hematopoietic cells, pathological cells or normal cells. In an embodiment in which the M4 meals have both M2 and M3 hematopoietic cells, the xenogeneic hematopoietic cells from mammal M3 may replace one or all of the hematopoietic deficiencies of mammal M2.

In one aspect of the present invention, it has been discovered that a normal, nude (athymic), transgenic, or other suitable non-human mammal M1, may have its hematopoietic and/or immune system substantially destroyed and replaced by a hematopoietic and/or immune system derived from bone marrow or other hematopoietic cells or cell lineages, such as peripheral blood leukocytes (PBLs), of a hematopoietic deficient non-human mammal M2, such as of the same species or genus of mammal M1, to provide a mammal M1–M2 having a normally functioning hematopoietic system optionally except for specific deficiencies of the hematopoietic system of the hematopoietic deficient donor mammal M2. The mammal M1–M2 may then be engrafted with xenogenic cells from a mammal M3 to provide a chimeric M4.

For example, when M1 is a normal mouse or rat and M2 is an hematopoietic deficient mouse, the obtained M1–M2 has a normally functioning hematopoietic system except for lack of B cells, T cells and their precursors. Due to the deficiency of the hematopoietic system of the donor mammal M2 and the resultant "empty space", e.g., lack of T and/or B cells, and/or precursors thereof in the thymus and/or bone marrow, in the mammal M1–M2, the cell types which are lacking can be gradually occupied by, and/or populated with, additionally engrafted normal human or other mammalian hematopoietic cells derived from human or other mammal M3, to provide a chimeric mammal M4 having hematopietic cells from both M2 and M3.

Alternatively, the resulting mammal M1–M2, lacking specific hematopoietic cells or cell lineages, is susceptible to engraftment of at least one cell lineage or tissue type from a xenogeneic mammal M3, such that the resulting mammal M4 having such transplanted or engrafted cells provides a model for pathologic conditions involving such cells or tissue in a mammal M3, or, when the cells or tissue include antibody producing cells, the resulting mammal M4, immunized with a specific antigen, will produce M3 antibodies, such as human antibodies where M3 is a human.

For example, the hematopoietic deficient non-human mammalian bone marrow from a mammal M2 may be combined with human or a different non-human mammalian bone marrow and/or other hematopoietic cell lineage, e.g., including both T cells and B cells, from a mammal M3 and transplanted into the non-human mammal M1 whose hematopoietic system has been substantially destroyed. The resulting chimera M4 can thus be used as a model of human immune response, a source of human antibodies, or as a model of human pathologies involving T cells or B cells.

It has also been discovered that the hematopoietic cells from a hematopoietic deficient non-human mammal M2 can promptly reconstitute all hematopoietic lineages which have been substantially destroyed in the mammal M1, except for those specific lineages in which mammal M2 is naturally deficient, such as the non-limiting example of T and/or B lymphocytic lineages in SCID mice, which specific lineages cannot develop from hematopoietic deficient mammal pluripotent stem cells, due to the deficiency in rearrangement of antigen receptor genes.

The reconstitution of the M2 hematopoietic deficient hematopoietic cells in a mammal M1 whose immune system has been substantially destroyed has been discovered to remove or substantially reduce the genetic and/or physiological defects of known hematopoietic deficient mammals, while at the same time allowing the possibility of transplantation of xenogeneic cells or tissue. An example of such a defect is the fact that, SCID mice suffer from DNA repair deficiencies as well as immune deficiencies. By transferring bone marrow of a SCID mouse into a normal irradiated animal, the engrafted chimera M1–M2 will have only the SCID hematopoietic deficiency, but will not suffer from DNA repair deficiency in all organs, other than in the hematopoietic system.

The treatment for substantially destroying the hematopoietic cells of mammal M1 may include irradiation (e.g., X-ray or gamma irradiation), chemotherapy, cytoreduction with antibodies directed against hematopoietic cells originating from mammal M1, thymectomy, or a combination thereof, or any other known method, provided that the treatment substantially eliminates the capacity of hematopoietic cells of M1 origin to successfully compete with the transplanted hematopoietic cells derived from mammal M2 and possibly mammal M3.

In all of the embodiments of the present invention, it is important that the immune system, i.e., the hematopoietic cells, of the animal being treated, be substantially destroyed. It is understood, however, that it is often inevitable that some hematopoietic cells survive the treatment and the present invention comprehends this eventuality. As long as the number of hematopoietic cells of M1 origin which survive are insufficient to compete with the new hematopoietic cells being transplanted from mammal M2, and possibly cells also from mammal M3, then the M1 hematopoietic cells are considered to be "substantially destroyed".

If sufficient hematopoietic cells remain after the treatment to permit the animal to survive under normal laboratory conditions, then there will be sufficient hematopoietic cells remaining to compete with the transplanted hematopoietic cells and interfere with the present invention. Thus, those of ordinary skill in the art will understand that the term "substantially destroy" means to either completely destroy the M-1 hematopoietic cells of the mammal M1 being treated or to leave such a small number of surviving hematopoietic M1 cells that the animal could not survive under normal laboratory conditions, where such a small number of surviving hematopoietic M1 cells is of insufficient quantity to compete with the transplanted hematopoietic cells from M2 and/or M3. Thus, the term "substantially destroyed" is not intended to comprehend a sublethal treatment, such as a sublethal dose of radiation, where the hematopoietic cells of the mammal M1 are not substantially destroyed, such as more than 10, 15 or 20% surviving after 4 weeks. Preferably, after such treatment of mammal M1 to substantially destroy M1's hematopoietic cells, a sufficiently small quantity of the treated mammal M1's hematopoietic cells remain in the bone marrow and peripheral blood such that no more than about 10% M1 T cells can be found in the peripheral blood of the mammal M4 (or M1–M2) four weeks after transplant.

A lethal dosage of radiation usually requires a cumulative dosage of 4–50 Gy (1 Gy =100 RAD), or any value or range therein, which is sufficient to substantially destroy the hematopoietic cells of the particular mammal M1 being irradiated. The specific dose which will be effective in any specific instance will depend on the species and condition of mammal M1. Furthermore, the lethal irradiation may be a single irradiation dose or a fractionated dose, i.e., a plurality of irradiation treatments, each separated by one or more of days. As non-limiting examples, an irradiation dosage of more than about 10 Gy and a fractionated protocol of 4 Gy on day 1 and 9–10 Gy three days later, have been found to substantially destroy the hematopoietic system of BALB/c mice, used as mammal M1.

Another way to determine if the conditioning protocol has caused the hematopoietic cells of the mammal M1 to be substantially destroyed is to measure the relative quantity of M1 T cells in the peripheral blood of the mammal M4 (or the mammal M1–M2) four weeks after transplant. An inverse correlation has been found between the percent of M1 T cells in the peripheral blood four weeks after transplant and the survival of the xenogeneic cells in mammal M4. If more than about 10% M1 cells are present, it is unlikely that the M4 transplant will be successful. If greater than about 10%, the treatment to that point will have been insufficient to substantially destroy the M1 hematopoietic cells. If the amount of M1 cells exceeds about 10%, it is still possible to treat the mammal, for example, with anti-M1-T cell antibodies, in order to bring the amount of M1 T cells in chimera M4 below about 10%. Another technique to help ensure that the amount of M1 T cells in the peripheral blood of M1–M2 or M4 four weeks after transplant is below about 10% is to thymectomize the mammal M1 prior to irradiation.

As discussed above, it is known from previous studies of murine bone marrow transplantation (for review, see, van Bekkum, D. W. et al. (1985) *Bone Marrow Transplantation: Biological Mechanisms and Clinical Practice*, Dekker, New York) that, following lethal doses of total body irradiation, some host hematopoietic cells survive the conditioning protocols. Other hematopoietic cells can be generated by surviving early progenitor cells, which have retained their ability to differentiate and proliferate despite the massive doses of radiation or chemotherapy. Since the present invention comprehends the possibility of a relatively small number of such host-type lymphocytes or other hematopoietic cells remaining after destruction, they will occasionally be found in the chimetic mammals of the present invention. For this reason, care must be taken to characterize the chimera's cells for the desired xenogeneic phenotypes as well as testing the xenogeneic origin of antibodies produced by the chimeras.

The present invention also relates to the production and use of a chimeric non-human mammal M1–M2, comprising a mammal M1 whose hematopoietic cells have been substantially destroyed and replaced by hematopoietic cells from a hematopoietic deficient mammal M2. The resulting chimera M1–M2 can be used, inter alia, as pathogen or xenogeneic human cell or tissue recipients to provide animal models of human pathologies.

In a preferred embodiment of the present invention, the transplanted xenogeneic cells or tissue in the mammal M4, or the meal M1–M2, have long-term stable stability. The term "long-term stable," as used herein, is intended to refer to transplanted cells or tissue which survive, grow, divide and/or differentiate in a mammal M4 or M1–M2 of the present invention for a reasonable period of time. Preferably, such transplanted cells are stable for a period of longer than about 1–4 weeks, more preferably longer than about 30 days, and most preferably for more than about four months and ideally through the entire life span of the resulting chimeric animal. Stability of transplanted xenogeneic hematopoietic cells can readily be determined by detection of xenogeneic antibodies in the peripheral blood. For example, if human hematopoietic cells M3, containing B cells, are transplanted into a mouse M1 in accordance with the present invention, the continued production of human antibodies in M4 is evidence of survival of the transplanted hematopoietic cells. Such human antibody production often continues for more than about four months. Survival of transplanted cells or tissue other than hematopoietic cells, such as tumor tissue, can more readily be directly determined.

The present invention enables prolonged survival of the chimeric mammals of the present invention, such as human-normal mouse or rat chimera, even when kept in a non-sterile environment, both prior to and after hematopoietic cell transplantation. It further provides an abundance of human T cells, the target of HIV infection, in these animals, and the prolonged survival of these cells in vivo in the mammal M4 of the present invention. Thus, such chimeric mammals may be used as animal models for at least some aspects of the study of HIV infection, activity and treatment.

The mammal M1 can be any non-human mammal that is capable of having its hematopoietic cells substantially destroyed and replaced by hematopoietic cells from a hematopoietic deficient mammal M2, such that the transplanted M2 hematopoietic cells remain viable and replicate in the resulting M1–M2 mammal, while the mammal M1–M2 also allows transplantation, engraftment and growth of cells from a xenogeneic mammal M3 in the resulting mammal M4, without appreciable rejection of the M3 transplanted cells or their progeny.

The non-human mammal M1 may be a normal mammal, a nude mammal, a transgenic mammal, a chimetic mammal, a gene-deficient mammal, or a mutant strain of a non-human mammal. A mammal M1 my include, inter alia, non-human mammals having normal hematopoietic systems and/or cells, deficient hematopoietic cells other than of a SCID mammal, transgenic cells, cells from two or more syngeneic, allogeneic or xenogeneic mammals or gene-deleted cells from any cell source, such as another mammal, cell culture, tissue culture, including primary, transformed, recombinant, fusion or mutated cells.

The non-human mammal M1 of the present invention may be any mammal, such as a horse, sheep, or rodent, such as, for example, mouse, rabbit, hamster, guinea pig, rat, and the like, although it is preferably a mammal conventionally used as a laboratory animal, most preferably a rat or a mouse.

An example of a transgenic or gene-deleted mammal is a mouse lacking the $\beta_2$-macroglobulin gene, which is unable to express major histocompatibility antigens (mouse H-2 antigens) on the cell surface. See, e.g., Overburgh et al., (1991) *J. Biol. Chem.* 266:16903–16910.

In some cases, the non-human mammal recipient M1 may also be an animal which already has a genetically determined or determinable hematopoietic deficiency, thus providing as recipient an animal likely to be even more immunosuppressed after treatment to substantially destroy its hematopoietic cells, than normal mice.

Mammals M1 and M2 may be of different species but preferably are of the same order or genus, such as a species or genus of the order Rodentia (e.g., as a rat, a mouse, a hamster, a guinea pig, a rabbit, etc.). In some preferred embodiments, M1 is a mouse and M2 is a SCID mouse or M1 is a rat and M2 is a SCID mouse.

According to the present invention, any non-human mammal with any immune or hematopoietic deficiency may be used as mammal M2. Such hematopoietic deficiencies may include genetic hematopoietic deficiencies or any induced or discovered hematopoietic deficiency. Generally, such mammals may have hematopoietic deficiencies due to mutation, selective breeding, genetic engineering, chemical, antibody or irradiation treatment, or as a result of selective transplantation of hematopoietic cells from other hematopoietic deficient mammals, such as chimera including hematopoietic deficient cells or tissue. Chemical, monoclonal or irradiation treatment of normal or hematopoietic deficient mammals followed, optionally, by at least one transplantation or retransplantation into syngeneic, allogeneic or xenogeneic mammals, to provide mammals having one or more hematopoietic or immune deficiencies. The hematopoietic deficiency may also be physically induced such as by serial transplantation, by physical removal of long-term stem cells, such as CD34 cells, or by any other such technique. It is known, for example, from Jones R. J. et al., (1989) Blood 73:397–401, that serial transplantation of bone marrow can cause the marrow to exhaust its long term self-renewal capability. Similarly, it is known from Jones, R. J. et al. (1990) *Nature* 347:188, that physically separating long term stem cells, such as by means of elutriation, prior to transplantation, will produce a short term chimera. Separation of long term stem cells can also be achieved by adherence to stroma (see Verfaillie, C. et al. (1990) *J. Exp. Med.* 172:509–520), or by removal of $CD34^+$ stem cells such as by means of an anti-CD34 antibody. Such serially transferred bone marrow or physically separated bone marrow can be used as the M2 cells having a hematopoietic deficiency. For the purpose of the present invention, hematopoietic cells taken from a mammal M2 without a hematopoietic deficiency but treated prior to transplant to create a hematopoietic deficiency therein will also be considered to fall within the definition of "hematopoietic cells derived from a mammal M2 having a hematopoietic deficiency".

A hematopoietic deficient mammal M2 is preferably of the same species, genus or order as M1 and preferably has a condition in which it is depleted of T and B cells, such as the non-limiting examples of Bg/Nu/Xid (BNX), Nu, Bg, SCID mice, or any combination or mutation thereof.

As a non-limiting example, useful mammal strains having hematopoietic deficiencies include SCID, Bg, Nu, Xid and $W/W^v$ mice, or any combination thereof, such as Bg/Nu/Xid (BNX mice). Gene-deleted or transgenic mammals created so as to have a genetically determined hematopoietic deficiency will also be suitable for use as mammal M2 according to the present invention. In another example, normal mice (e.g., BALB/c) may be lethally irradiated and transplanted with hematopoietic cells from mammals of the same species, such as normal bone marrow, followed by serial transplantation of such transplanted cells into other lethally irradiated normal BALB/c mice one or more additional times, such that the resulting mice will have hematopoietic deficient hematopoietic cells having limited self-renewal capacity, suitable as M2 donors. Alternatively, the hematopoietic cells to be transplanted may be treated to remove populations of specific cells, such that long term renewal of such cells is substantially reduced or eliminated. Such treatments may include the use of cell separation, such, as for example, removal of $CD34^+$ cells.

Non-limiting examples of the types of hematopoietic deficiencies which may occur in a mammal M2 making it suitable for use in the present invention, are: a deficiency in rearrangement of antigen receptor genes (such as C, V, J, V-J, J-C, V-J-J or V-J-C genes in maturing B cells); defective antigen presenting cells; defective antigen processing;, defective B cell differentiation, proliferation, and/or maturation; defective T cell differentiation, proliferation and/or maturation; defective cytokine receptors; defective T suppressor cell, macrophage or antibody (Ab) regulation of B cell maturation or Ab production; overproducing of natural anti-idiotypic antibodies which prevent B cell or T cell maturation or production of Abs by blocking B cell or T cell receptors; defective T cell receptors; defective T cell receptor chain rearrangement; or other such abnormalities.

The preferred source of hematopoietic cells from mammal M2 is bone marrow, either untreated or depleted of T cells. Other suitable sources of hematopoietic cells which may also be used include, for example, spleen cells, fetal liver cells or peripheral blood cells, which may be cultured or non-cultured, along with supporting stromal cells. Thus, the hematopoietic cells transplanted from mammal M2 may be selected or derived from at least one of:

(i) unfractionated or fractionated bone marrow cells;
(ii) unfractionated or fractionated blood cells;
(iii) unfractionated or fractionated spleen or thymus cells;

(iv) unfractionated or fractionated cord blood cells;
(v) unfractionated or fractionated fetal cells (liver, thymus, bone marrow, spleen or blood); and
(vi) any combination thereof.

As described herein and as would be clear to the skilled artisan based on the teaching and guidance presented herein, hematopoietic deficient (e.g., immuno-deficient), non-human meals M2 are used according to the present invention as hematopoietic cell donors so that at least one hematopoietic lineage may be rapidly reconstituted. Such reconstituted hematopoietic cell lines or lineages, from hematopoietic deficient mammal M2 alone or possibly with those from mammal M3, may thus be detected in peripheral blood of transplanted mammals M4 shortly after transplant and are long-term stable thereafter.

The mammal M3 may be any non-human or human mammal, non-limiting examples being human, rodent (mouse, rat, hamster, guinea pig, rabbit or other rodent), primate, horse, pig, cow, lamb, dog, cat, or other mammal, wherein M3 is of a different species than M1. In the preferred embodiment, mammal M3 is a human or another mammal for which cures to veterinary diseases are being sought, such as livestock, i.e., ovine, bovine, canine, feline and equine animals.

There are two major embodiments of chimeric non-human mammals of the present invention. The first embodiment is a chimeric mammal M4, in which the xenogeneic cells or tissue derived from mammal M3 are hematopoietic cells transplanted in order to permit a long-term stable xenogeneic hematopoietic cells, or at least portions thereof, to be present in the mammal M4. This embodiment is useful, for example, to insert xenogeneic immune system cells into a laboratory animal so as to be able to obtain xenogeneic antibodies, e.g. monoclonal antibodies, or other xenogeneic immune response from that laboratory animal. Such mammals may also be used as models of the effects of drugs or other therapy on the xenogeneic hematopoietic cells of the laboratory animal. Specific hematopoietic or other immune system abnormalities which occur in a given species, such as humans, may also be created in the laboratory animal to allow such laboratory animals to serve as models for those pathologies, or to allow production of antibodies to antigens which otherwise might not be immunogenic in the species.

In a second major embodiment of chimeric meals of the present invention, the xenogeneic cells or tissue obtained from mammal M3 are other than hematopoietic cells. Such xenogeneic cells or tissue may be normal tissue, such as human liver tissue, which may be transplanted into a laboratory animal to serve as a model of human liver diseases, such as hepatitis, etc. Such xenogeneic cells or tissue may also be pathological tissue, e.g., hepatitis C virus-infected liver cells, or malignant tissue which, when long-term stably transplanted into a laboratory animal, will allow that animal to provide a model for the effects of various treatments for such pathologies or malignancies. Indeed, in a preferred example, the cells or tissue which are transplanted into the laboratory animal in accordance with the present invention are the pathological cells or tissue of the specific patient to be treated so as to determine the effects of such treatment in a laboratory animal model before using it on the patient.

In the embodiment in which the cells or tissue derived from mammal M3 are hematopoietic cells, the source of such hematopoietic cells may be any suitable source of such cells. Thus, the hematopoietic cells transplanted from mammal M3 may be selected or derived from at least one of:
(a) unfractionated or fractionated adult or fetal bone marrow cells;
(b) unfractionated or fractionated adult or fetal blood cells;
(c) unfractionated or fractionated cord blood cells;
(d) unfractionated or fractionated adult or fetal thymus, spleen or lymph node cells; and
(e) any combination thereof.

Unfractionated or fractionated bone marrow cells may include, e.g., T cell-depleted, or different cell populations of the myeloid, erythroid, megakaryocytoid or lymphoid lineages and their precursors and/or combinations thereof. Unfractionated or fractionated blood cells may include, e.g., subpopulations of different lymphocytes, macrophages, monocytes, platelets or erythrocytes and their precursors and/or combinations thereof. Preferably, fractionated blood cells are used which are human peripheral blood leukocytes (PBL). Pluripotent stem cells and/or other hematopoietic progenitors derived from B cell-depleted and T cell-depleted peripheral blood leukocytes may also be included.

The type of xenogeneic hematopoietic cell lineage expressed in the chimeric mammal M4 will depend on the nature of the hematopoietic deficiency of the mammal M2, since transplanted pluripotent stem cells of xenogeneic origin and originating from mammal M3, may reconstitute the "empty space" in the reconstituted population resulting from the hematopoietic deficiency of mammal M2. The inability of hematopoietic cells of mammal M2 to generate that lineage allows it to be replaced by cells of the corresponding xenogeneic hematopoietic lineage from mammal M3. As mammal M2 in one preferred embodiment is of the same species or genus as mammal M1, or at least much closer than mammal M3, it is expected that in all respects other than the genetic deficiency, the hematopoietic cells from mammal M2 will normally regenerate after the BM transplantation to reconstitute these lineages and thereafter will predominate over the corresponding cells from mammal M3.

The outcome of the competition between human hematopoietic lineages and the mouse hematopoietic lineages can be tilted in favor of the human cells by the use of the above short-term hematopoietic precursors having limited self-renewal capacity, by use of cytokines acting specifically on human cells, by transplantation of human stromal cells, and/or by using a transgenic recipient mammal M1 having genes expressing human cytokines, according to known method steps.

Other human hematopoietic cell lineages, such as the erythroid, myeloid, granulocyte, macrophage and megakaryocytoid lineages, may be reconstituted in the mammal M1 according to the present invention, depending on the particular deficiency of mammal M2, yielding different types of chimeras.

The chimeric mammal M4 of the present invention may be used as an experimental model for the study of a variety of human or veterinary diseases, as well as for other purposes. As a non-limiting example, when xenogeneic cells from mammal M3 are human T and B cells which are used to provide a chimera M4, such a non-human chimeric mammal M4 may be used for, as sub-non-limiting examples: (1) production of human monoclonal antibodies or cytotoxic T cells against a variety of antigens, such as those associated with pathogens (e.g., viruses or toxins), as well as the production of autoimmune cells, pathological cells (e.g., cancer cells), or pathological or normal blood cells; (2) the induction of tolerance towards human leukemic cells in animals transplanted with bone marrow from leukemia patients and then infused with the patient's leukemic cells; (3) production of human T cell lines, lymphokine-activated killer (LAK) cells or cytotoxic T lymphocytes (CTLs)

directed against human malignancies or other pathologies; (4) study of human T and B cell ontogeny, which is presently limited largely to in vitro systems; and (5) as animal models for AIDS and other viral disease, by infection of the chimeric mammal with HIV-1 or other viruses.

In the embodiment in which the xenogeneic cells or tissue from mammal M3 are other than hematopoietic cells, the cells and/or tissue from mammal M3 may include, as non-limiting examples, normal or pathological animal cells or tissue, such as cerebrospinal fluid (CSF), cells or internal and external secretions of skin, heart, lung and respiratory system, liver, spleen, kidney, pancreas, ovary, testis, brain, gall bladder, gastrointestinal tract, smooth, skeletal or cardiac muscle, circulatory system, reproductive organs, auditory system, the autonomic and central nervous system, and extracts or cell cultures thereof, provided in vivo, in situ or in vitro, as cultured, passaged, non-passaged, transformed, recombinant, or isolated cells and/or tissue. Such cell or tissue, as non-limiting examples, may include nerve tissue, liver cells, kidney cells, muscle cells, heart cells or myocardial cells, arterial or venous cells or tissue, connective tissue or cells, lung tissue or cells, spleen tissue, endocrine tissue or cells, or cells of the central nervous system.

As a non-limiting example, the mammal M3 may be a human and the M3 pathological cells and/or tissue may be human malignant cells for providing a mammal M4 as a cancer chimetic mammal model. Indeed, the human tissue or cells which are transplanted may be primary tumors or metastatic tissue dissected by surgery, or leukemic cells. The human or other mammalian tissue from M3 may be obtained from healthy or unhealthy subjects (such as those having any known pathologic state, e.g., hepatitis C, and grafted into mammal M1 as small pieces, such as by placement under the kidney capsule of mammal M1.

Chimeric Animal Models of Human or Primate Pathologies

Using the present invention, it is possible to test compounds or biomolecules for efficacy against human pathological cells or tissue, such as those established from fresh specimens removed during surgery or obtained by any other means. As a non-limiting example, tumors from the vast majority of human cancer patients may grow in a human-:mouse chimera of the present invention.

Accordingly, the use of human pathological or normal control cells or tissue in a non-human chimeric mammal will allow the testing of a large number of new drugs against various pathologies, under conditions approaching in vivo testing in humans. In addition to testing new drugs for therapeutic activity, it will be possible to test established chemotherapeutic agents and their combinations for specific therapeutic activities against various pathologies of an individual, to identify the most effective agents to treat such a patient.

Thus, the present invention also relates to the use of a non-human mammal M4 obtained from a non-human mammal M1 having its hematopoietic cells replaced by hematopoietic cells of a hematopoietic deficient (e.g., immunodeficient), non-human mammal M2, preferably of the same species, genus and/or order of M1, resulting in a hematopoietic deficient, e.g., immunodeficient, mammal which can be further transplanted, engrafted, or administered with cells and/or tissue from a mammal M3 of a species other than M1 and M2, which cells and/or tissue are provided to obtain a mammal M4 which is a chimeric model of a pathology of mammal M3 or as a control chimeric model of a normal condition of mammal M3. Preferably, mammal M3 is a human and the pathologies and/or normal controls are human pathologies and/or controls.

Such pathologies may include, but are not limited to, viral pathologies that are related to the liver or to immune deficiencies, cancer involving particular cell or tissue types, bacterial or viral infection or toxin exposure in which the host response involves the cellular immune system, trauma or drug side effects that cause immunosuppression of specific cell or tissue types, or other pathologies that involve specific sets of hematopoietic cells.

Such related pathologies my include, but are not limited to, cancers such as breast cancer, leukemias, tumorigenesis, lung cancers, colon cancers, brain cancers, etc.; virus infection, such as hepatitis (e.g., HCV) adenovirus (e.g., E1b), SV40, papillovirus (e.g., E6), TAg, etc.; virus related cancers such as cervical carcinoma (herpes virus2), Kaposi's sarcoma (cytomegalovirus), Burkitt's lymphoma and nasopharyngeal carcinoma (Epstein-Barr virus) and T-cell lymphoma (retrovirus); or other pathologies involving cytoplasmic sequestration of p53. See, e.g., Chabner et al, (1990) eds., *Cancer Chemotherapy: Principles and Practice*, Lippincott); De Vita et al., (1985) eds., *Principles and Practice of Oncology*, 2nd Edition; Salmon, (1991) In: *Current Medical Diagnosis and Treatment*, Schroeder et al., eds., Appleton and Lange; Sartorelli et al., (1981) eds., *Molecular Actions and Targets for Cancer Chemotherapies*, Academic Press, (1981); Katsung (1992), *Basic and Clinical Pharmacology*, Appleton and Lange, Norwalk, Conn., which references are herein incorporated entirely by reference.

Such viral infections include, but are not limited to the viral diseases listed in Table 12-1 of Berkow et al (1992) eds., *The Merck Manual*, 16th edition, pp. 77–86, 182–220, 2166–2203, Merck and Co., Rahway, N.J.; and Katsung, supra, pages 674–681 and references listed therein on pages 680–681, which references are entirely incorporated herein by reference.

Bacteria produce endotoxins and enterotoxins which are known to cause shock in humans, which can result in death. Such bacteria include, e.g., enterotoxigenic *E. coli* (ETEC), enterohemorrhagic *E. coli* (such as strains of serotype 0157:H7), Shigella (*S. dysenteriae, S. flexmeri, S. Boydii*, and *S. sonnei*), Salmonella (*S. typhi, S. cholera-suis, S. enteritidis*), Clostridium (*C. perfringens, C. difficile, C. botulinum*), Camphlobacter (*C. jejuni, C. fetus*), Heliobacter, (*H. pylori*), Aeromonas (*A. sobria, A. hydrophila, A. caviae*), *Pleisomonas shigelloides, Yersina enterocolitica*, Vibrios (*V. cholerae, V. parahemolyticus*) which produce endotoxins and/or enterotoxins which affect humans and other animals. Such bacterially related pathologies may thus include, but are not limited to, gastroenteritis, enterocolitis, diarrhea, fever, hypotension, dehydration, lung congestion and collapse, abdominal distension, mucosal hemorrhage, intestinal and smooth muscle inflammation, leukocytosis, septicemia, hepatitis, neuromuscular poisoning, cramps, vomiting, nausea, and related symptoms. See, e.g., Stein, (1990) ed., *Internal Medicine*, 3rd ed., pp 1–13, Little, Brown and Co., Boston; Evans et al., (1991) eds., *Bacterial Infections of Humans: Epidemiology and Control*, 2d. Ed., pp 239–254, Plenum Medical Book Co., New York; Mandell et al (1990) *Principles and Practice of Infectious Diseases*, 3d. Ed., Churchill Livingstone, New York (1990); Berkow et al, supra; the contents of which references are incorporated entirely herein by reference.

Accordingly, the introduction of an M3 mammalian cell or tissue to produce a mammal M4 as a chimeric animal model of an M3 mammal pathology or M3 normal control, according to the present invention, provides the ability to test therapeutic and/or diagnostic agents for such pathologies.

A therapeutic agent may be any known agent having a therapeutic effect on a target cell, such effect being selected from, but not limited to: correcting a defective gene or protein, a drug action, a toxic effect, a growth stimulating effect, a growth inhibiting effect, a metabolic effect, a catabolic affect, an anabolic effect, an antiviral effect, an antibacterial effect, a hormonal effect, a neurohumoral effect, a cell differentiation stimulatory effect, a cell differentiation inhibitory effect, a neuromodulatory effect, an antineoplastic effect, an insulin stimulating or inhibiting effect, bone marrow stimulating effect, a pluripotent stem cell stimulating effect, an immune system stimulating effect, and/or any other known therapeutic effects that may be provided by a therapeutic agent administered to a chimeric non-human mammal according to the present invention.

Besides the administration of a therapeutic agent, any other therapeutic modality may also be tested on such animal models of the present invention, such as application of irradiation, heat, or any other physical treatment that is found to have a potential therapeutic effect.

The diagnostic agent may be detectably labeled as for labeling antibodies, as described herein. Such labels include, but are not limited to, enzymatic labels, radioisotope or radioactive compounds or elements, fluorescent compounds or metals, chemiluminescent compounds and bioluminescent compounds. Alternatively, any known diagnostic agent can be used in a method of the present invention.

As another non-limiting example, a chimeric mammal M4 of the present invention, having malignant tumor cells from M3 as a human, may be used as an experimental model for the study of a variety of human solid tumors and leukemias, providing a tool for chemotherapy sensitivity testing of drugs or any therapeutic or diagnostic agent.

In a further embodiment, IL-2 activated peripheral blood mononuclear cells, also referred to as lymphokine activated killer cells (LAK) (Rosenberg, S. A. et al., (1985) *J. Exper. Med.* 161:1169–1188 and (1987) *now Engl. J. Med.* 316:899–941; Lotze, M. T. et al., (1980) *J. Immunol.* 125:2972–2978; Lotze M. T. et al., (1981) *Cancer Res.* 41:4420–4425; Grimm, E. A. et al., (1983) *J. Exper. Meg.* 158:1365–1371), or tumor infiltrating lymphocytes (TIL) (Rosenberg, S. A. et al., (1988) *N. Engl. J. Meg.* 319:1676–1680), may be transplanted into a mammal, e.g. a mouse, M4 bearing a human tumor, so as to test the efficacy of the LAX or TIL cells in immunotherapy, optionally together with a cytokine, such as IL-2.

Use of Transgenic Non-Human Mammals for the Production of Chimeric Animal Models:

The mammal M1 may be a transgenic non-human mammal (preferably a rodent, such as a mouse) whose germ cells and somatic cells contain DNA which encodes human proteins of interest, for example human MHC antigens or human cytokines, lymphokines or growth factors, such as IL-1, IL-1β, IL-2, IL-3, IL-4, IL-5, IL-6, IL-7, IL-8, IL-9, IL-10, IL-11, interferons (α, βγ), TNFs (α, β), TGFs (α, β, γ), GM-CSF, M-CSF, G-CSF, EPO and the like, which influence the growth and differentiation of hematopoietic cells from hematopoietic precursors and stem cells. The DNA is introduced into the animal, or an ancestor of the animal, at an embryonic stage, preferably the one-cell, or fertilized oocyte, stage, and generally not later than about the 8-cell stage. The activated sequence, as the term is used herein, means a gene which, when incorporated into the genome of the animal, is expressed in the animal.

There are several means by which such a "transgene" can be introduced into the genome of the animal embryo so as to be chromosomally incorporated and expressed. One method is to transfect the embryo with the gene as it occurs naturally, and select transgenic animals in which the gene has integrated into the chromosome at a locus which results in expression. Other methods for ensuring expression involve modifying the gene or its control sequences prior to introduction into the embryo. One such method is to transfect the embryo with a vector containing an already modified gene. Other methods are to use a gene the transcription of which is under the control of an inducible or constitutively acting promoter, whether synthetic or of eukaryotic or viral origin, or to use a gene activated by one or more base pair substitutions, deletions, or additions.

Introduction of the desired gene sequence at the fertilized oocyte stage ensures that the transgene is present in all of the germ cells and somatic cells of the transgenic animal and has the potential to be expressed in all such cells. The presence of the transgene in the germ cells of the transgenic "founder" animal in turn means that all its progeny will carry the transgene in all of their germ cells and somatic cells. Introduction of the transgene at a later embryonic stage in a founder animal may result in limited presence of the transgene in some somatic cell lineages of the founder; however, all the progeny of this founder animal that inherit the transgene conventionally, from the founder's germ cells, will carry the transgene in all of their germ cells and somatic cells.

Chimeric non-human mammals in which fewer than all of the somatic and germ cells contain the desired human DNA, produced, for example, when fewer than all of the cells of the morula are transfected in the process of producing the transgenic mammal, are also intended to be within the scope of the term "transgenic mammal" as used herein.

The techniques described in Leder, U.S. Pat. No. 4,736,866 and Palmiter et al., (1986) *Ann. Rev. Genet.*, 20: 465–99 (which references are hereby incorporated by reference in their entirety) for producing transgenic non-human meals may be used for the production of the transgenic non-human mammal which may be uses as a starting material (mammal M1) of the present invention.

A preferred transgenic mouse M1 that can be used according to the present invention is a transgenic mouse bearing human HLA histocompatibility antigens, for example a (BALB/c×C57BL/6)$F_1$ mouse expressing human HLA-B7 genes (prepared as described by Hammerling, G. J. et al. (1990), *Proc. Natl. Acad. Sci.* USA 87:235–239, hereby incorporated by reference), or a transgenic mouse bearing genes expressing one or more different human cytokines, such as IL-3, IL-6, G-CSF, GM-CSF, and the like.

Alternatively, the transgenic mammal or gene deleted mammal M1 may be a mammal lacking the $\beta_2$-macroglobulin gene, which is unable to express major histocompatibility antigens (e.g., in mouse, mouse H-2 antigens) on the cell surface. See, e.g., Overburgh et al., (1991) *J. Biol. Chem.* 266:16903–16910.

It should be understood that the present invention is not drawn to techniques of producing transgenic animals and such transgenic mammals are only used as starting materials in the methods of the present invention. No new techniques of producing transgenic animals are disclosed herein. Those of ordinary skill in the art are already aware of the existence of many types of transgenic animals and already have the knowledge to produce additional transgenic animals having characteristics which would make them desirable for use as a recipient mammal M1 or possibly a donor mammal M2 or M3.

Human Monoclonal Antibody Production:

The present invention also provides for the production of human monoclonal antibodies by immunizing a non-human mammal M4 of the invention having human B cells with a specific antigen to induce the production of human antibody-producing cells, such as mature B cells, which produce human monoclonal antibodies specific for the antigen. The antibody producing cells may then be immortalized and cloned to provide cells which produce human monoclonal antibodies in recoverable and/or commercially useful amounts, according to known method steps such as, but not limited to, hybridomas, EBV transformation, or cloning of antibodies in animal cell lines. See, e.g., Ausubel et al. *Current Protocols in Molecular Biology*, Greene Publ. Assoc. and Wiley Interscience, NY, N.Y. (1987, 1993), Harlow et al. (1988) *Antibodies: A Laboratory Manual*, Cold Spring Harbor Laboratories, N.Y., Page et al. (1991) *Bio/Technology* 9:64–68 and Borrebaeck (1989) *J. Immunol. Meth.* 123:157–165.

As a non-limiting example, the preparation of human monoclonal antibodies in accordance with the present invention comprises immunizing the non-human chimeric mammal M4 having human B cells with an antigen to induce human antibody forming cells in the chimeric mammal in recoverable amounts, removing antibody-forming cells from the spleen or any other appropriate site from the immunized mammal, fusing the suspended cells with a suitable fusion partner to produce hybridomas, appropriately diluting and culturing the cells in separate containers, screening the supernatant in each container containing a hybridoma for the presence of antibody, and selecting and cloning the hybridoma for the presence of antibody, and selecting and cloning the hybridomas producing the desired antibody. These procedures are performed by well-known techniques, described in the literature. See, e.g., Kohler and Milstein,(1975) *Nature* 256:495–497; U.S. Pat. No. 4,376,110; Ausubel, supra; and Harlow, supra; and Coligan et al. (1992, 1993) *Current Protocols in Immunology* Green Publishing Assoc. and Wiley Interscience, the contents of which references are incorporated entirely herein by reference.

The antigen may be any antigen, for example, a virus, a protein, a peptide, a normal or pathological cell, a nucleic acid, another organic compound (such as a drug or prodrug), an inorganic compound, and the like (see, e.g., Harlow, supra, and Ausubel, supra, Coligan, supra). The hybridoma fusion partner may be of human origin or of non-human mammal origin. In a preferred embodiment, the fusion partner is a mouse myeloma cell, a human myeloma cell or a fused mouse:mouse or mouse:human myeloma cell.

In order to produce the desired monoclonal antibody, the hybridoma cells are either cultured in vitro in a suitable medium, and the desired monoclonal antibody is recovered from the supernatant, or the hybridoma cells are injected intraperitoneally into mice, and the antibodies harvested from the malignant ascites or serum of these mice, according to known method steps, see, e.g., Harlow, supra, Ausubel, supra, Coligan, supra.

Also included in the present invention are antibodies and antibody producing cells and cell lines, such as hybridoma, EBV transformed, or recombinant antibody expressing cells or cell lines producing such antibodies, provided according to known method steps.

While this section relates to the production of human monoclonal antibodies, it will, of course, be understood that the production of monoclonal antibodies of other mammal can be produced in the same manner. For example, if ovine or bovine monoclonal antibodies are desired for use in treating veterinary diseases, they may be produced in a similar manner in laboratory animals by using an ovine or bovine donor mammal M3 instead of a human.

Human:Non-Human Mammal Human Viral Diseases Chimeric Animal Model

In another embodiment, the non-human chimeric mammal M4 is used as an animal model for AIDS or other human viral diseases, e.g. hepatitis C, caused by viruses which infect humans but do not normally infect mice. Such murine infection with the human virus is now possible because the chimeric mammal M4, in contrast to normal mammal, may be created with human T cells in its blood or tissue which are susceptible to infection and/or response to the human virus in the chimeric mammal. For this purpose, a chimeric mammal M4 may be infected with a human virus, such as HIV-1 or another AIDS-inducing virus, by injection of the appropriate virus isolate using methods well-known in the art (Namikawa et al. (1988) *Science* 242:1684). About 2–3 weeks later, the infected animal is tested for the presence of viral antigen, such as an HIV-1 antigen (e.g., gp120, gp41 and the like) in the blood. If the animal is HIV-positive, it has been successfully infected and may then be used as a convenient test system for (a) evaluating new agents thought to be active against the virus infection, such as HIV infection, or (b) for studying the efficacy and bioavailability of either known (e.g., AZT) or new drugs against the viral disease. Other viruses for which the present invention is useful include, but are not limited to, HIV-2, HTLV-I, HTLV-II, adenovirus, SV40, papillovirus, TA9, and the like.

In one embodiment, human bone marrow cells from mammal M3 used for transplantation into mammal M1 can be rendered resistant to HIV infection by genetic manipulation (gene therapy) prior to transplantation. The efficacy of such gene therapy can then be evaluated in the chimeric M4 mammal model.

Such a chimeric mammal M4 of the present invention having human tissue may also be used as an experimental model for the study of a variety of human specific diseases, such as virus infections and autoimmune diseases, being a useful tool for screening, sensitivity testing and monitoring of drugs for the diseases. Thus, grafting of human liver tissue will establish a model for study of hepatitis B and C; grafting of thymus, spleen or lymph nodes tissue will enable the study of AIDS; and grafting of pancreas tissue will establish a model for diabetes mellitus. For study of hepatitis C, a chimeric mammal M4 is engrafted with liver tissue of a hepatitis C patient and, after 2 weeks, the animal is tested by PCR for hepatitis C virus (HCV) antigen (5'-non coding region).

As indicated above, veterinary diseases can also be studied in laboratory animal models by substituting the particular veterinary animal cells or tissue for human tissue in the above discussion.

Cytotoxic T cell production to specific pathologic cells.

The present invention also relates to methods for producing human or other mammalian cytotoxic T cells (CTL) against a pathogenic antigen, for use in therapeutic or diagnostic applications. In this embodiment, a chimeric non-human mammal M4 having stable xenogeneic CTL precursor cells derived from a mammal M3, is immunized with pathological cells, tissue or components thereof presenting an antigen capable of eliciting the cytotoxic T cells in recoverable amounts in the mammal M4. The CTLs which are produced may then be recovered from the immunized mammal M4. The recovered CTLs are capable of providing a therapeutic effect against the pathology caused by such cells by lysing the pathological cells or tissue. Preferably, the M3 pathological cells and the CTL precursor cells are from the same human or mammal. The pathological cells may be cancer or virally infected cells.

Having now generally described the invention, the same will be more readily understood through reference to the following examples which are provided by way of illustration, and are not intended to be limiting of the present invention, unless specified.

EXAMPLE I

Engraftment of Human T and B Lymphocytes into Lethally Irradiated BALB/c Mice The experiments were performed as follows. Eight to 12 week-old female BALB/c mice (obtained from Olac Farms, Bicester, England) were exposed to a single dose of 10 Gy TBI from a Gammabeam 150-A $^{60}$Co source (produced by the Atomic Energy of Canada, Kanata, Ontario) with a focal skin distance (F.S.D.) of 75 cm, at a 0.7 Gy/min dose rate. One day later, $10\times10^6$ T cell-depleted human bone marrow cells were transplanted intravenously into each mouse. These bone marrow cells have been prepared by differential agglutination with soybean agglutinin, followed by E-rosetting with sheep red blood cells, as described by Reisner et al. (1981), *Lancet* ii:327. Twenty-four hours after infusion of the human bone marrow cells, T cell-depleted bone marrow from 8- to 12 week-old male SCID mice (Weizmann Institute Animal Breeding Center, Rehovot, Israel) was prepared according to Reisner et al., (1978) *Proc. Natl. Acad. Sci.* USA 75:2933, with minor modifications (Schwartz, E. et al., (1987) *J. Immunol.* 138:460), and $2\times10^6$ cells were transplanted.

For analysis, mice were bled from the retro-orbital vein, using heparin-coated glass capillaries, at different time intervals, and mononuclear cells were purified by Ficoll-Hypaque fractionation. The presence of human T and B cells was detected using detectably labeled monoclonal antibodies. Anti-T cell antibodies included anti-neu4 (anti- CD3), anti-Leu3 (anti-CD4), and anti-Leu2 (anti-CD8) (Becton-Dickinson, Mountain View, Calif., USA). Anti-B cell antibodies included B1 (anti-CD20) and B4 (anti-CD19) (Coulter Immunology).

Total human Ig content in the serum of transplanted mice was evaluated 3 to 8 months post-transplant by using a double-antibody ELISA. Microtiter plates were coated with 100 μl of affinity- purified goat anti-human Fab' antibodies (50 μg/ml) (BioMakor, Ness Ziona, Israel). Non-specific binding of protein was eliminated by incubation in a 7% solution of bovine serum albumin (BSA) in PBS for 2 hours. Diluted (1:1) serum from transplanted mice (50 μl) was then applied to each well for 16 hours at 4° C. The wells were washed and incubated for 2 hours at 37° C. with peroxidase-goat anti-human Ig (IgG, IgM, IgA) (Zemed Laboratory, Calif.), which was incubated with the same volume of normal mouse serum before its final dilutions (to avoid cross-reactivity with Mouse Ig). Following additional washes, substrate solution [2,2- azinodi-(3-ethylbenzthiazoline sulfonic acid) diammonium salt (ATBS)] (Sigma, USA) was applied. The optical density at 620 nm was determined by a Titertek Multiscan-ML (Flow Laboratories) ELISA reader. Total Ig concentrations were calculated by reference to a standard curve with purified human Ig. Readings corresponding to more than 20 ng/ml were recorded as positive. This threshold was based on control experiments in which sera of mice transplanted with SCID bone marrow alone was negative. Human IgG and IgM were determined in some mice (see text) as described above, using as second antibodies peroxidase-horse anti-human (IgG)Fc (BioMakor) and peroxidase-goat anti-human IgM(μ) (BioMakor).

The results of the experiments are summarized in Table I.

TABLE I

Engraftment of Human T- and B-Lymphocytes Into Lethally Irradiated BALB/c Mice

| | Weeks after | | Mice with human lymphocytes (or Ig) in peripheral blood[a] | | | |
|---|---|---|---|---|---|---|
| Expt. | Transplant | Survival | T | B | T + B | Human Ig[b] |
| 1 | 7 | 7/10 | 1/7 | N.T. | | |
| 10 | 7/10 | 4/7 | N.T. | | | |
| 16 | 7/10 | 7/7 | N.T. | | | |
| 22 | 7/10 | 6/6 | 6/6 | 6/6 | 6/6 | |
| 2 | 7 | 3/6 | 0/3 | N.T. | | |
| 18 | 3/6 | 2/3 | 1/3 | 1/3 | 0/3 | |
| 3 | 9 | 7/8 | 4/7 | 4/7 | 4/7 | 3/7 |
| 4 | 11 | 4/7 | 3/4 | 4/4 | 3/4 | 1/4 |
| 5[c] | 11 | 7/8 | 6/7 | 5/7 | 5/7 | 2/7 |
| 6[d] | 11 | 8/14 | 3/8 | 7/8 | 2/7 | 5/8 |
| 7[e] | 12 | 7/7 | 5/7 | 7/7 | 5/7 | 1/7 |

[a]number of positive mice/total
[b]total human Ig content in the serum of transplanted mice was evaluated 3 to 8 months post-transplant by using a double-antibody ELISA.
[c]Unseparated bone marrow ($80 \times 10^6$ cells per mouse, intravenously)
[d]Unseparated bone marrow ($200 \times 10^6$ cells per mouse, intraperitoneally)
[e]Mononuclear bone marrow cells ($15 \times 10^6$ cells per mouse, intravenously)

As can be seen in Table I, this approach has led to the development of human T and B cells in the peripheral blood of lethally irradiated normal BALB/c mice, which are H-2 identical with the SCID bone marrow donors. A total of 31 mice in 4 series of experiments received transplants of $10\times10^6$ SBAE human bone marrow cells by the intravenous route, followed one day later by an intravenously-administered transplant of $2\times10^6$ T cell- depleted bone marrow cells from SCID mice. Of the 31 mice transplanted, 20 have survived for at least 3 months and up to more than 8 months. Mortality due to infection (10 mice out of 31) was observed mainly during the first 3 weeks post-transplant; one mouse died of infection during the fifth month post-transplant, following bleeding from the retro-orbital vein. Mice were periodically bled in order to assess engraftment of human lymphocytes in peripheral blood lymphocytes (PBL). Sixteen of the 20 survivors were found to be engrafted with human T cells, and/or human B cells. In 14/20 surviving mice, both T and B lymphocytes of human origin have been detected in significant numbers in the peripheral blood, beginning as early as 7 weeks and extending to up to 9 months post-transplant.

EXAMPLE II

Quantitative evaluation of T cell engraftment

A quantitative evaluation of T cell engraftment during the post-transplant period is best illustrated by the first series of mice, which have been observed for more than 6 months (FIG. 1). The appearance of human CD3$^+$ T cells in peripheral blood of transplanted mice was first documented in one mouse (No. 3) 7 weeks post-transplant (FIG. 1, inset). In this mouse, 25% of PBL bound a monoclonal antibody specific for human CD3, compared to 66% of normal human PBL. In this assay, only 0.9% of PBL obtained from a mouse transplanted with SCID mouse marrow alone, were labeled with this reagent.

By the tenth week post-transplant, low but significant numbers of T cells were found in 4 out of 7 mice tested, ranging from 6.5% to 10.8% (an average of 7.9%). A marked increase in T cell numbers was found by the end of the fourth month post-transplant, at which time all 7 mice were found to be engrafted with human $CD3^+$ T cells. In 6 out of 7 mice tested, the percentage of T cells present in peripheral blood was above 10%, ranging from 11.1% to 54.1% (an average of 27.1%).

Further phenotyping of the engrafted T cells with monoclonal antibodies specific for human CD8 and CD4 revealed abnormal or immature phenotypes, such as $CD3^+CD2^+$ $CD4^-CD8^-$ lymphocytes commonly found in leukemia patients early after successful bone marrow transplantation with T cell-depleted bone marrow (Keever, C. A. et al. (1989) *Blood* 79:1340). The percentage of these cells among the total human T cells in peripheral blood of engrafted mice 5 months post-transplant ranged from 49% to 84%. However, the remainder of the human T cells in peripheral blood were of mature phenotypes commonly found in normal peripheral blood, such as $CD3^+CD4^+CD^8$ and $CD3^+$ $CD4^-$ $CD8^+$.

Thus, unlike the study in which a transient human T cell engraftment was detected only during the first month post-transplant (McCune et al., supra), the experimental model of the invention demonstrates a slow but steady increase in human T cell numbers in peripheral blood of transplanted mice, beginning as early as 7 weeks post-transplant and reaching a plateau during the fourth and fifth months post-transplant (FIG. 1). These results are in accordance with the slow rate of T cell differentiation seen in human SCID and leukemia patients following transplantation of $SBA^-E^-$bone marrow (Reisner, Y. et al. (1983) Blood 61:341).

EXAMPLE III

Responsiveness of Engrafted Human T Cells to Mitogens

The responsiveness of engrafted human T cells to mitogens was evaluated by stimulation of splenocytes of human-mouse chimeras (from the third series) 5 months post-transplant, with a specific anti-human CD3 antibody, under conditions (OKT3/ATCC, Rockville, Md., USA, 1 μg–2 μg/well) used to test immune reconstitution in SCID or leukemia patients after bone marrow transplantation. This mitogen selectively stimulated human T cells and is not cross-reactive with murine cells. It is therefore more suitable than plant mitogens for evaluation of human-mouse chimeras.

Upon 7 days of culture with the mitogen, stimulation indexes were 3.1 and 2.2 in two chimeric mice tested, compared to 2.2 exhibited by human PBL and 0.8 by normal mouse splenocytes. However, the magnitude of the response of human-mouse chimeric splenocytes (the difference between the averages of thymidine incorporation obtained in the presence and in the absence of anti- OKT3) was only 10% (3178 cpm) and 7% (2440 cpm) respectively, of the normal human PBL response (32,707 cpm).

Figures 2A, 2B, 2C:
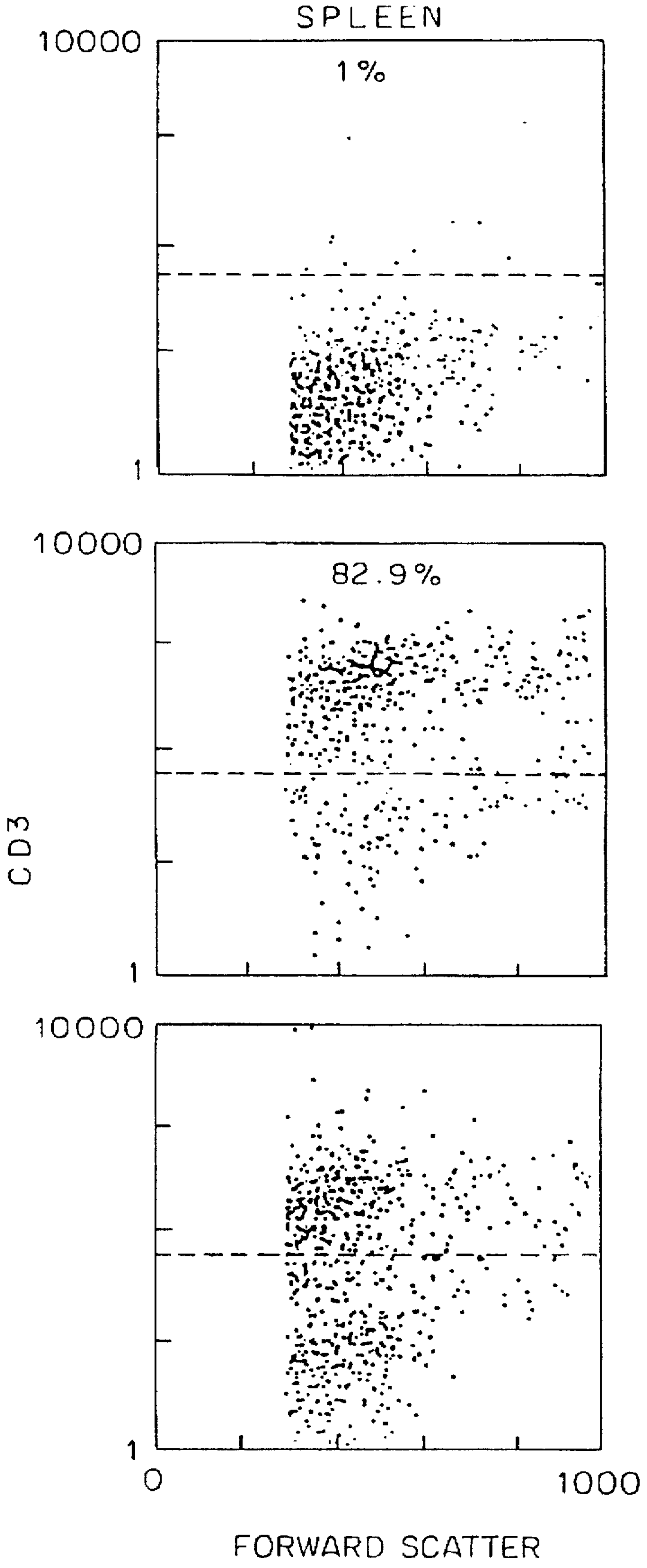
FIG. 2A–2C are representation showing the staining of human-mouse chimeric spleen cells with anti-human CD3 after 7 days of culture in IL-2-containing medium.

When spleen cells from the above chimeras were incubated with IL-2 containing medium and tested after 7 days of culture, by staining with anti-human CD3 antibody, human T cells were predominant (55%), in the surviving population, resembling the predominance of T cells observed when normal human PBL are cultured with these stimuli (83%) (FIG. 2A–2C), as opposed to results obtained with splenocytes from a control mouse transplanted with SCID bone marrow alone (1%). This shows that it is possible to clone human T cells from such human-mouse chimeras and thereafter, to test their specificity against the stimulating antigen.

EXAMPLE IV

Production of Human Ig against KLH-DNP

The function of engrafted human B lymphocytes has been assessed by testing levels of human immunoglobulins in the serum, and titrating human antibodies generated in response to KLH-DNP (keyhole-limpet hemocyanin conjugated to dinitrophenol). Among mice transplanted with $SBA^-E^-$ human bone marrow (which is depleted of both T and B cells), 7/20 engrafted mice were positive for human Ig. In further testing of sera from 4 mice positive for human Ig, human IgM was detected in 2 animals and human IgG in 2 other mice. In subsequent experiments, mice were also transplanted with unmodified bone marrow (Table 1, see later) and 8/22 of these mice were positive for human Ig; human IgM was detected in two mice and human IgG in the other 6 animals.

Figure 3:
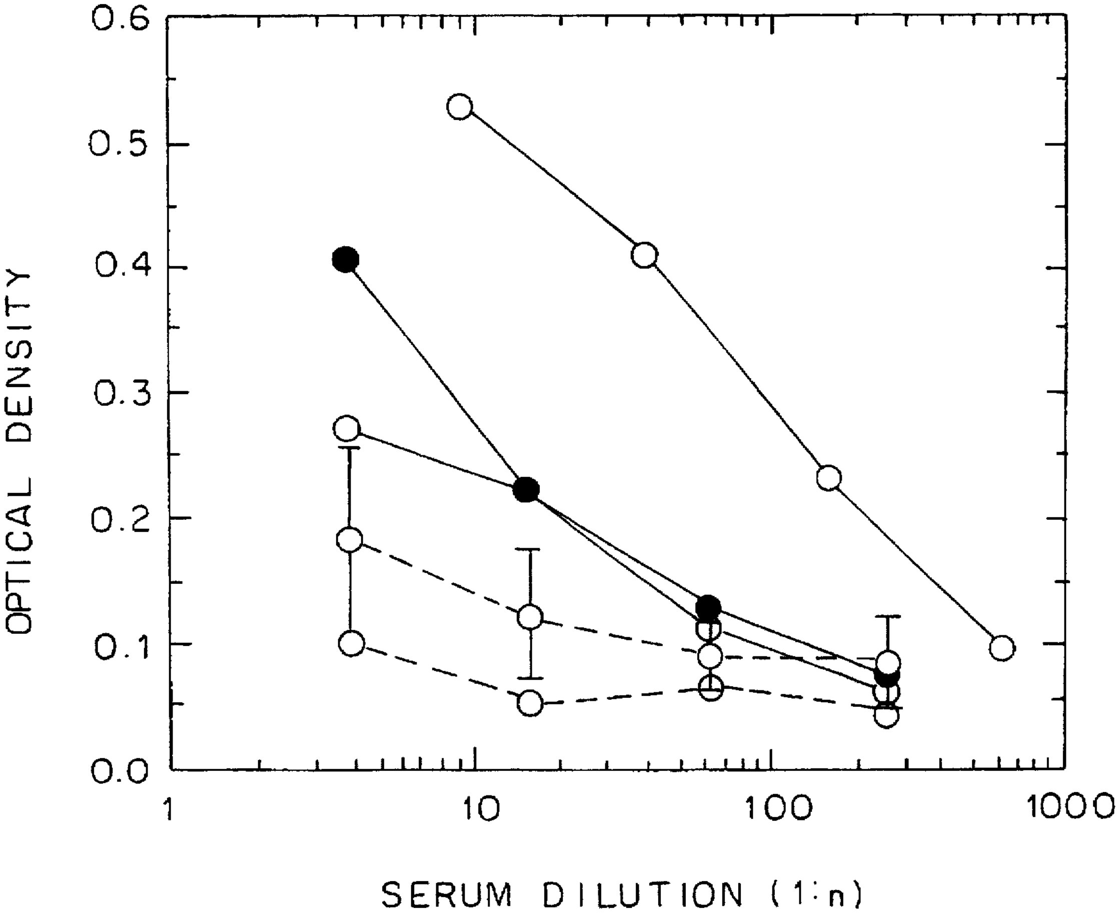
FIG. 3 is a graphical representation showing dinitrophenol (DNP)-specific human antibodies in a human-mouse chimera immunized with DNP-KLH. Human-mouse chimeras whose PBL included for both human T and B lymphocytes, and control mice transplanted only with SCID bone marrow cells, were immunized subcutaneously with 20 μg DNP-KLH emulsified in complete Freund's adjuvant. Forty-eight days later, some of the primed mice, as well as some unprimed transplanted mice, were injected subcutaneously with 100 μg DNP-KLH emulsified in complete Freund's adjuvant. Mice were bled 6 days later, and anti-DNP antibody was measured by ELISA, as described in the footnotes to Table 1, except that microtiter plates were coated with 100 μl/well of DNP-BSA (50 μg/ml). ○–○ sera of mice Nos. 2 (upper) and 3 (lower) from the first series (challenged twice). ●–● serum of a mouse from the third series (challenged once). ○- - -○ serum of a control mouse (challenged twice). ϕ- - -ϕ average (±standard deviation) of fifteen sera collected from control mice (transplanted with SCID bone marrow alone, and challenged once with KLH-DNP).

Immunization of chimeric mice positive for human Ig (2 mice from the first series and 2 mice from the third series, 8 and 6 months post-transplant, respectively) with KLH-DNP, has induced both primary and secondary responses specific for DNP in 2/4 animals (FIG. 3). Following secondary immunization, specific human IgG as well as IgM could be detected in one of two mice. These results suggest that engrafted human B lymphocytes are able to function in a murine environment.

EXAMPLE V

Analysis of Human DNA in Human:Mouse Chimera

Figure 4:
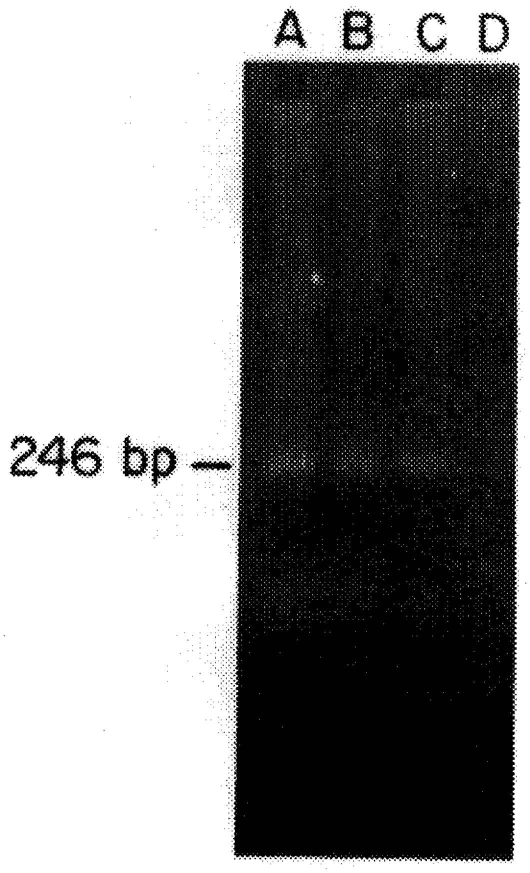
FIG. 4 is a representation of a gel pattern showing DNA analysis of peripheral blood cells from a human-mouse chimera 6 months post-transplant. PBL were lysed in distilled water and boiled for 10 min. Debris was sedimented by centrifugation, and the genomic DNA in the supernatant was amplified by the polymerase chain reaction (PCR) procedure for 30 cycles, using DNA polymerase from *Themus aquaticus* (Perkin Elmer-Cetus, Emeryville, Calif., USA) (Saiki, R. K. et al. (1988) *Science* 239:487). The reaction mixture, which included 500 ng genomic DNA, 20 pm of the DQB primers GLPDQB1 and GAMPDQB2 (Todd, J. A. et al., (1987) *Nature* 329:599) and 2 U Taq-DNA polymerase, was subjected to repeated cycles of denaturation at 94° C. for 30 sec., annealing at 56° C. for 30 sec. and extension at 72° C. for 30 sec. The products were analyzed by 2% agarose gel electrophoresis, where the amplification was regarded as successful only if the control sample from human PBL had a unique 246-bp band (Ronningen, K. S. et al., (1989) *Human Immunol.* 26:215). Lane A) normal human PBL; Lane B) an artificial mixture of human and mouse PBL (ratio 1:3); Lane C) PBL from a mouse transplanted with human bone marrow (mouse no. 1); Lane D) PBL from an untreated BALB/c mouse.

The presence of human lymphocytes in the peripheral blood of transplanted mice was further confirmed by DNA analysis. As can be seen in FIG. 4, genomic DNA of the human (HLA-DQβ) genes was detected in the peripheral blood of mouse No. 1, whereas a test of normal PBL from an untreated mouse yielded completely negative results. In the same sample of PBL from mouse No. 1 (taken 6 months post-transplant), cytofluorimetry using anti-CD3 and anti-CD19 monoclonal antibodies revealed the presence of 60% human T and B lymphocytes, while staining with an anti-$H2^d$ monoclonal antibody detected only 6.2% murine mononuclear cells.

EXAMPLE VI

Engraftment of Unmodified Bone Marrow

Transplantation of human bone marrow mononuclear cell populations which had not been depleted of T cells was performed using the same transplant approach, but with larger doses ($80\times10^6$ cells/mouse) of unmodified marrow (to provide a relatively comparable number of progenitor cells). A rate of engraftment similar to that achieved with T cell-depleted bone marrow (Table 1) and without manifestations of graft-versus-host disease was observed.

In summary, the present invention provides "normal" mice having human B and T cells, wherein a non-human normal mammal M1 has its hematopoietic cells substantially destroyed and replaced with hematopoietic cells of a human and of a hematopoietic deficient non-human meal.

EXAMPLE VII

Engraftment of Human PBL in Lethally Irradiated Mice

Figure 5A:
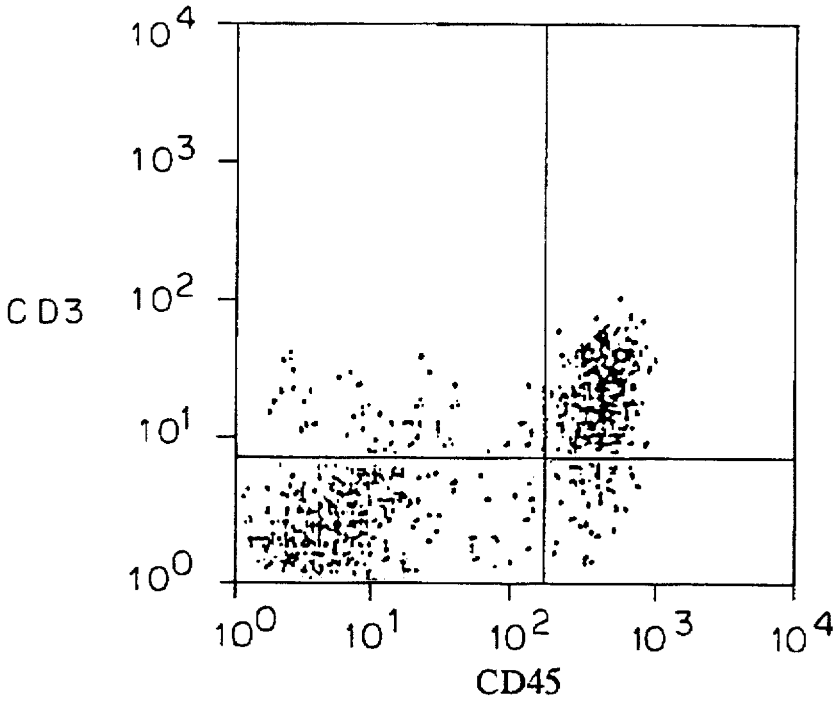
FIG. 5A–D is a graphical representation showing the double staining of peritoneal lymphocytes from a mouse transplanted with SCID bone marrow and human PBL using anti-human CD3 in combination with anti-human CD45 (FIG. 5A), and anti-human CD4 with anti-human CD8 (FIG. 5B). In control experiments, the same staining with anti-human antibodies was performed on peritoneal lymphocytes from mice transplanted with SCID bone marrow alone (FIG. 5C, D respectively).
Figure 5B:
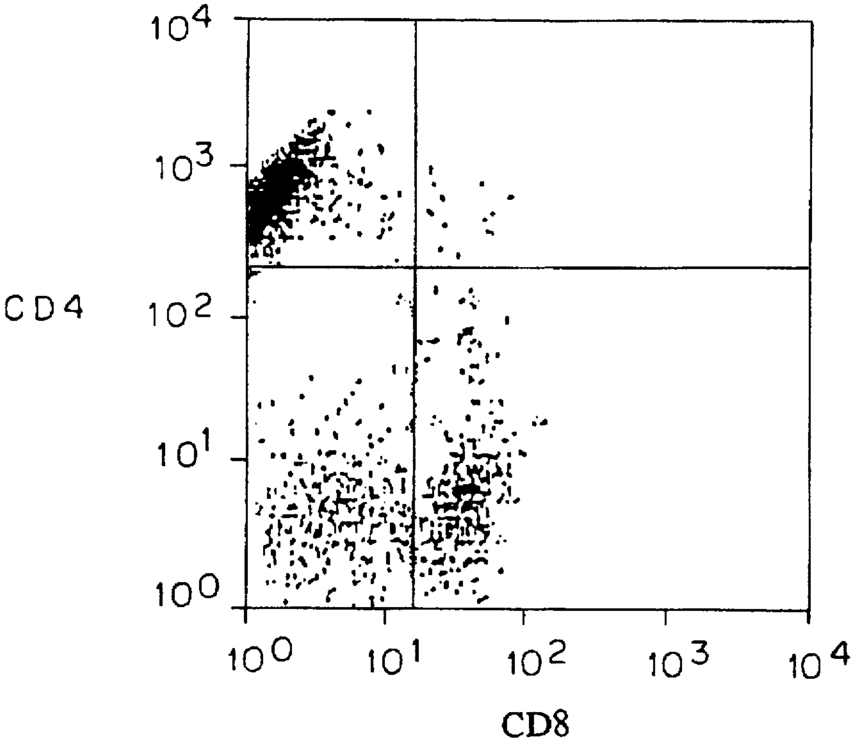
Figure 5C:
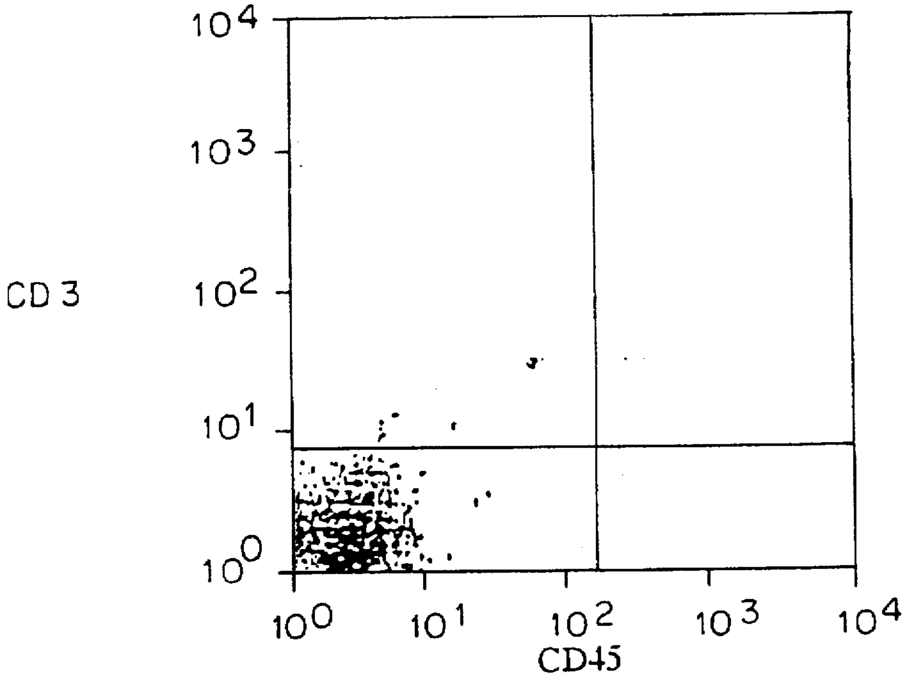
Figure 5D:
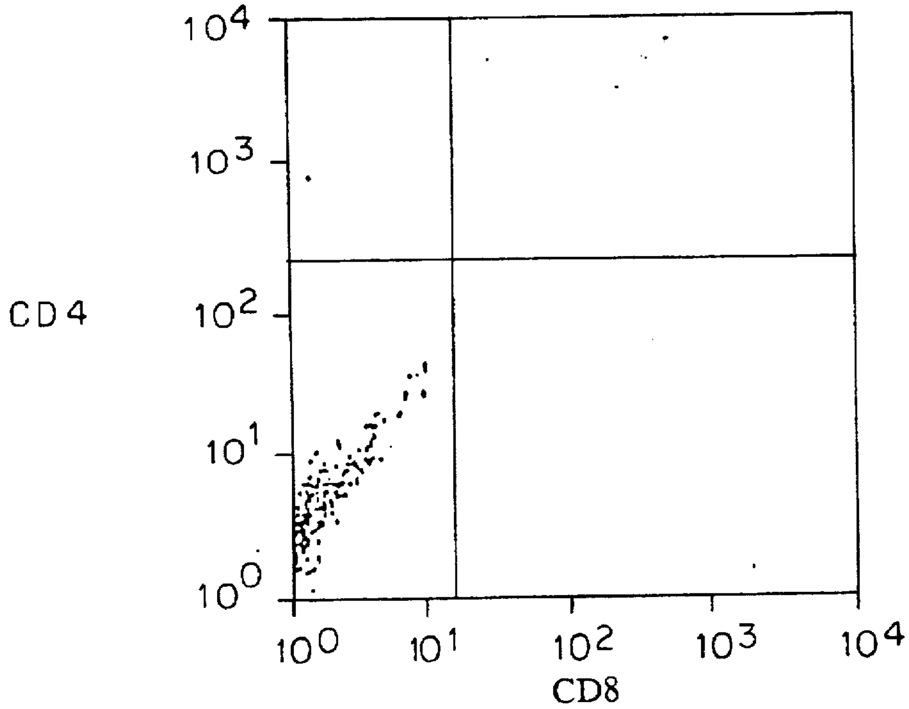
Figure 6A:
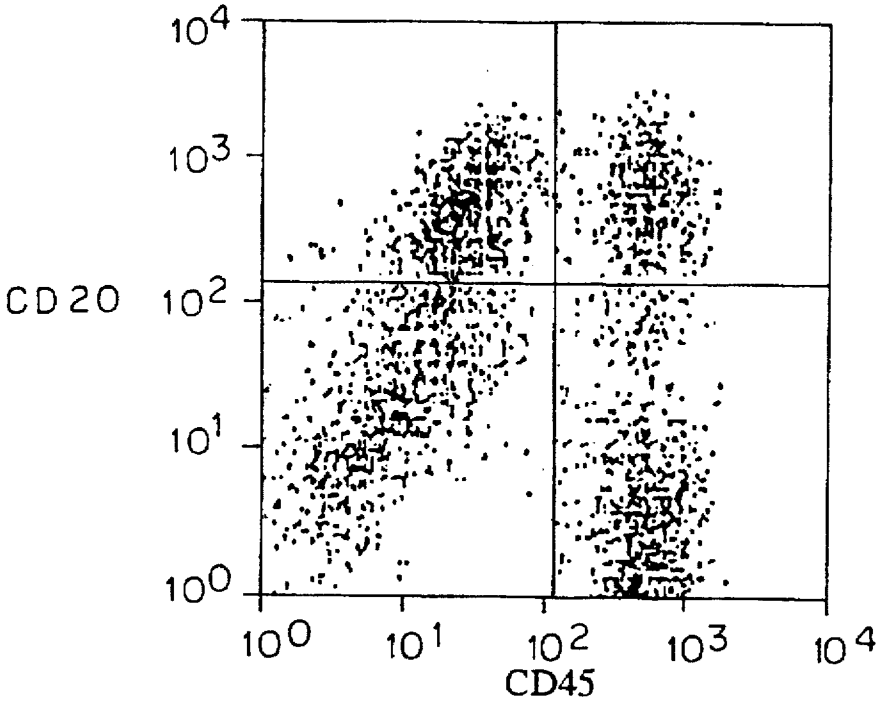
FIG. 6A–B is a graphical respresentation showing the double staining of peritoneal lymphocytes from a mouse transplanted with SCID bone marrow and human PBL using anti-human CD20 together with anti-human CD45 (FIG. 6A). In a control experiment, the same staining was performed on peritoneal lymphocytes from mice transplanted with SCID bone marrow alone (FIG. 6B).
Figure 6B:
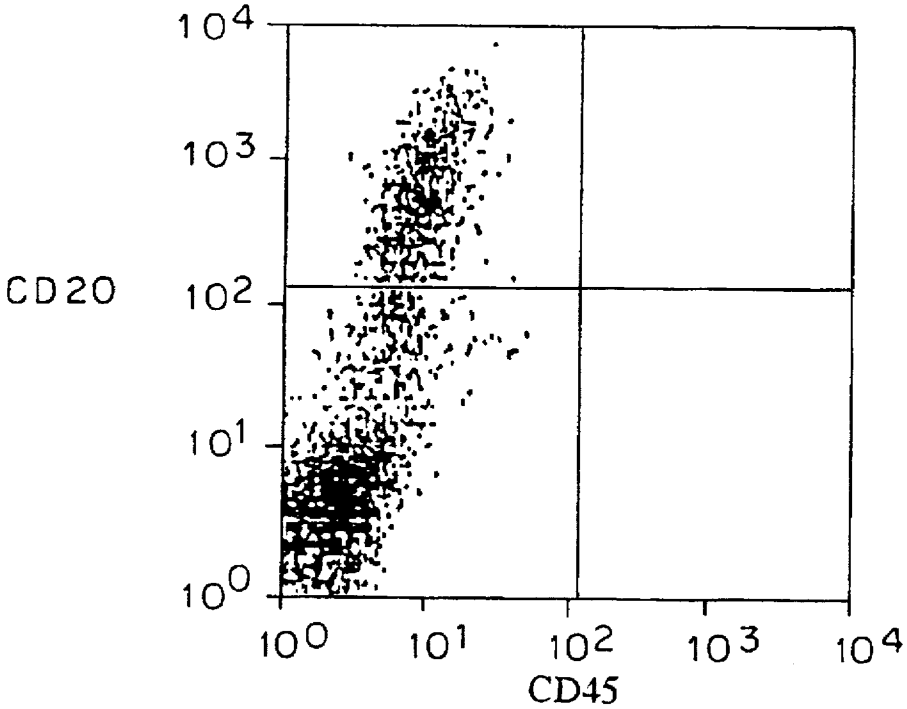

Eight to twelve-week old BALB/c mice were exposed to a total dose of 14 Gy TBI, an initial dose of 4 Gy followed after three days by a second dose of 10 Gy from a Gamma beam 150-A $^{60}$Co source with a focal skin distance of 75 cm, at 0.7/0.9 Gy/min. One day after the second dose, the mice were transplanted i.v. with T cell-depleted SCID bone marrow and 4–8×10$^7$ human PBL was administered intraperitoneally. Engraftment of human T cells was confirmed by double staining with anti-CD45 and anti-CD3 (FIG. 5A) and further characterized to include CD4 and CD8 T lymphocytes (FIG. 5B). The presence of human B lymphocytes was demonstrated by double staining with CD20 and CD45 (FIGS. 6A–6B). Production of human antibodies was evaluated by ELISA as described in Example IV and the data are presented in Table II. As can be seen from these results, human antibody production is superior in recipients of human PBL compared to recipients of human bone marrow.

EXAMPLE VIII

Engraftment of Human PBL in the Immune deficient BNX Mouse

Kamel-Reid and Dick (1988, *Science* 242:1706) attempted to graft human hematopoietic cells in the BNX mouse after conditioning with 4 Gy TBI. Engraftment was reported to be very low and required special cloning techniques to detect the presence of human precursors. We found similar poor engraftment of human PBL in such mice following 4 Gy TBI and therefore we used lethal TBI (e.g. 12 Gy) followed by i.v. transplantation of 1×10$^6$ T cell-depleted SCID bone marrow and intraperitoneal administration of 4–10×10$^7$ human PBL. The engraftment was characterized as described in Example VII and the significant improvement of engraftment can be seen both by the production of human Ig and by the cytofluorimetry analysis of human lymphocytes (Table III).

Figure 7:
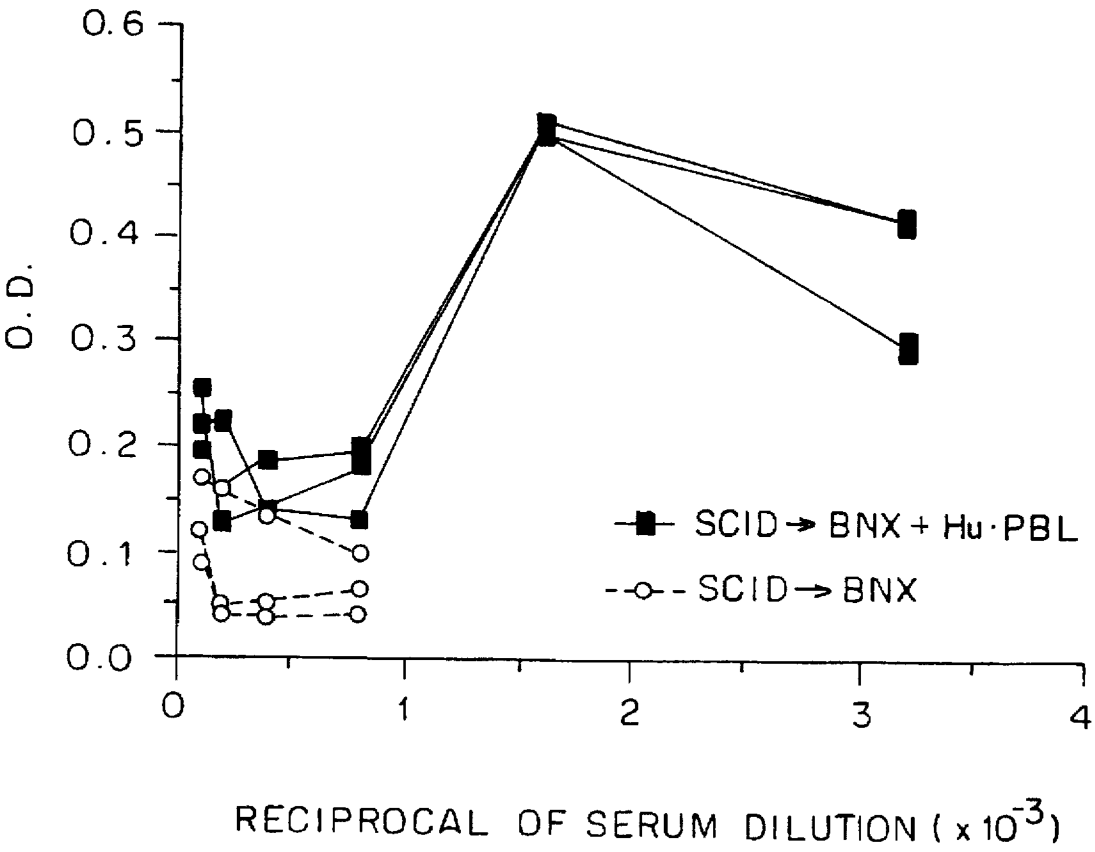
FIG. 7 is a graphical representation of human antibody production against a bacterial toxin antigen in a chimeric non-human animal of the present invention.

Furthermore, specific human antibodies have been generated to a peptide antigen of *Staphylococcus aureus* SEB (Staphylococcal Enterotoxin B), as shown in FIG. 7. In this experiment, BNX mice were given total body irradiation and then engrafted with SCID bone marrow. Some mice, represented by the solid lines, then received human PBL. Other mice, shown by dashed lines, did not. All mice were immunized with peptide SEB antigen, and the serum titers of human IgG and IgM specific to the peptide antigen, shown in optical density units, were determined.

Thus, it is shown that chimeric non-human mammals of the present invention can be used to produce human antibodies against specific antigens, and the human B cells producing such antibodies can be isolated and cloned or fused to produce hybridomas which can produce human monoclonal antibodies specific for the desired antigen.

EXAMPLE IX

Engraftment of Human PBL in Lethally Irradiated Rats

Figure 8A:
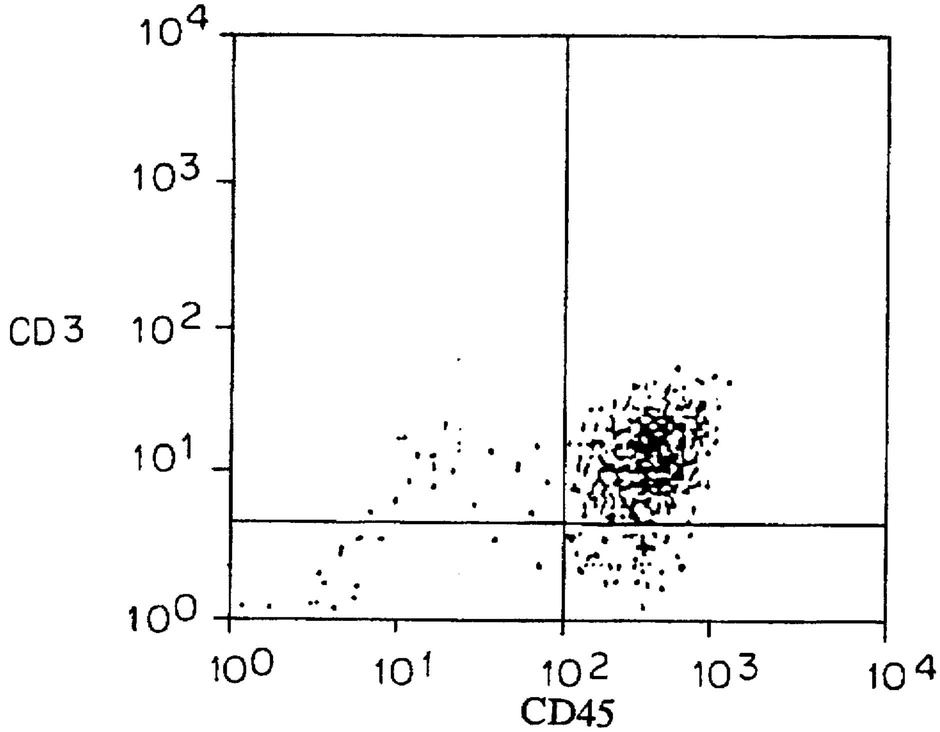
FIG. 8A–E is a graphical representation showing the double staining of peritoneal lymphocytes from a rat transplanted with SCID bone marrow and human PBL using anti-human CD45 together with anti-human CD3. In a control experiment, the same staining was performed on peritoneal lymphocytes from rats transplanted with murine SCID bone marrow alone (FIG. 8D). Erythrocytes from the same rat were stained by anti-H-$2^d$ (FIG. 8B) or anti-OX18 (FIG. 8C) rat class I histocompatibility antigens, in order to define what fraction of the newly formed erythrocytes is derived from the SCID bone marrow. In the control experiment for the erythrocytes, only the second antibody [FITC-conjugated $F(ab')_2$ fragment of goat anti-mouse IgG(Fc)] was used.
Figure 8B:
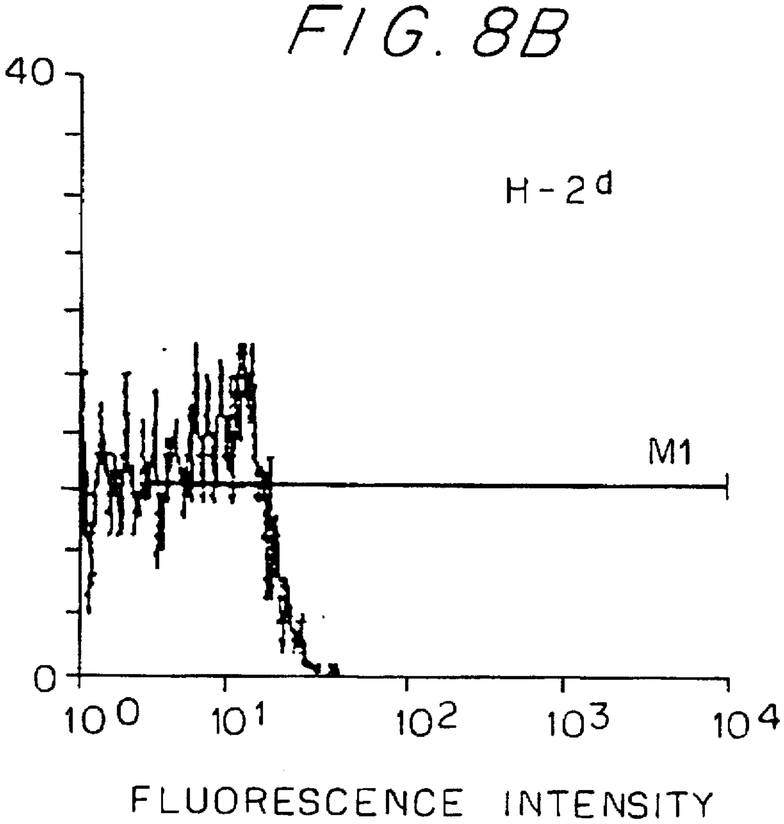
Figure 8C:
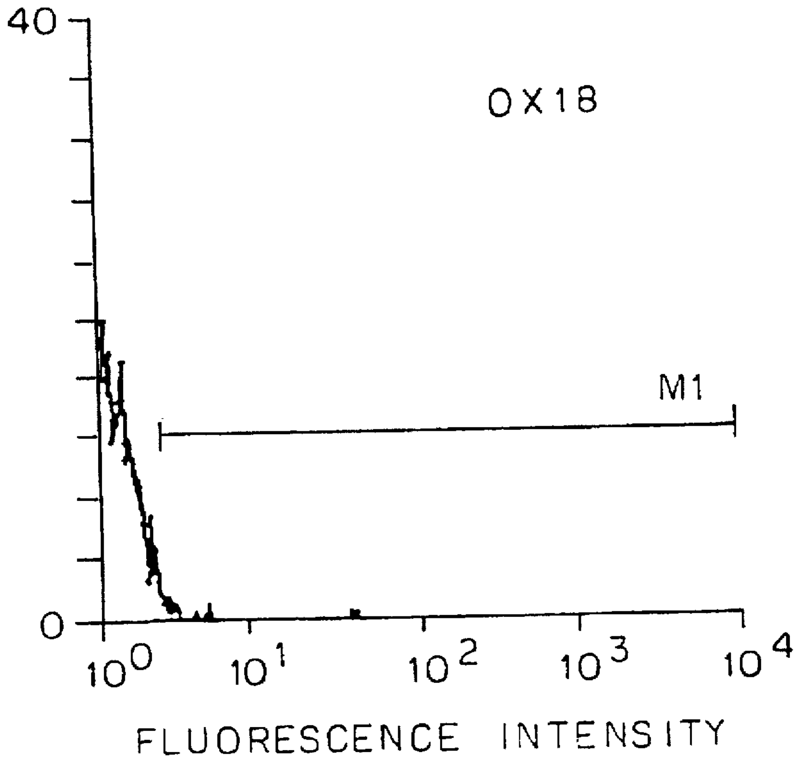
Figure 8D:
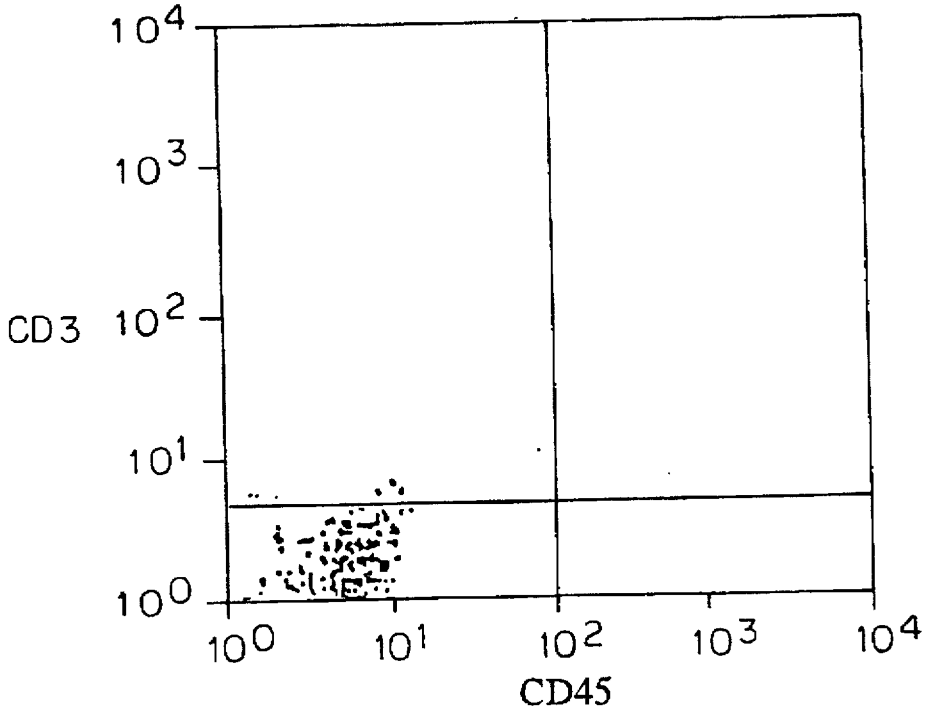
Figure 8E:
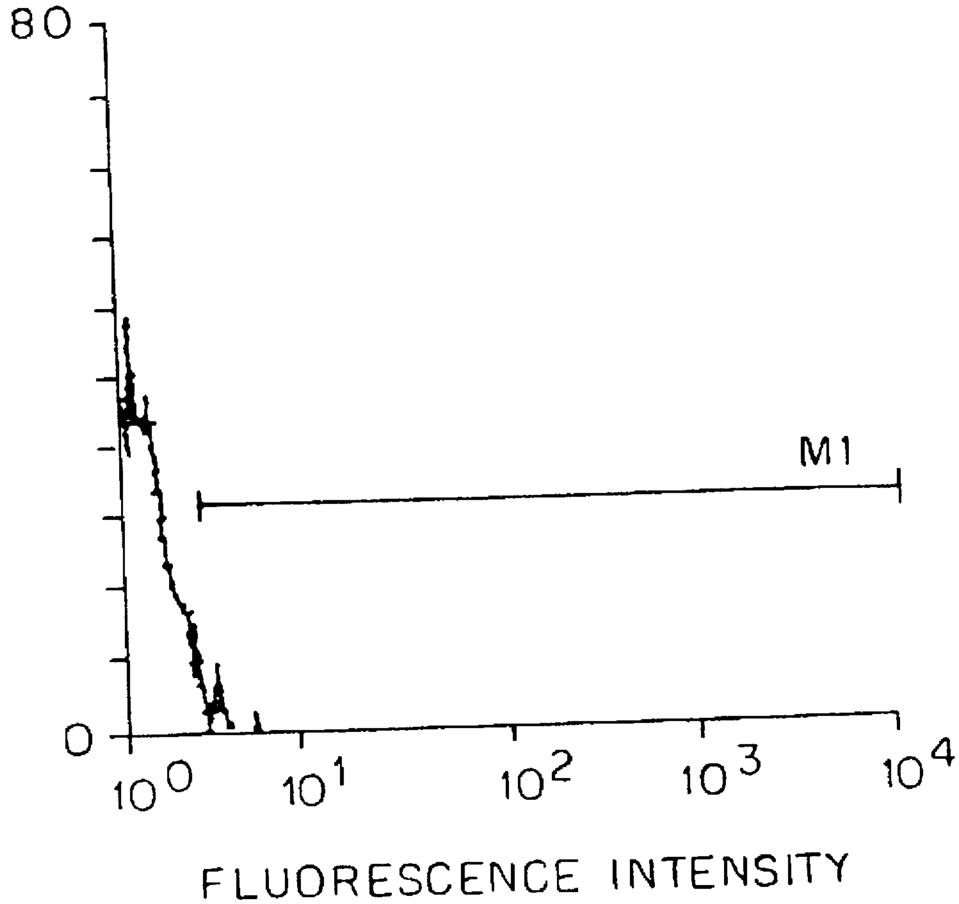

Lewis rats (4–8 weeks old), from the Animal Breeding Center at the Weizmann Institute of Science, were exposed to irradiation of 13 Gy TBI divided into two fractions: the first of 4 Gy and the second of 9 Gy three days later. The day following completion of the irradiation, the rats were treated with dimethyl myleran (0.5 mg i.v.) and a day later they were transplanted with 5–10×10$^7$ T cell-depleted SCID bone marrow i.v. and 3×10$^8$ human PBL intraperitoneally. Engraftment of human lymphocytes was documented 20 days after transplantation by double staining with CD45 and CD3 (FIG. 8A). A major fraction of the erythrocytes was shown to be of mouse origin, as documented by staining of histocompatibility antigens [H-2d for mouse origin (FIG. 8B) and 0X18 for those of rat origin (FIG. 8C)].

Figure 9A:
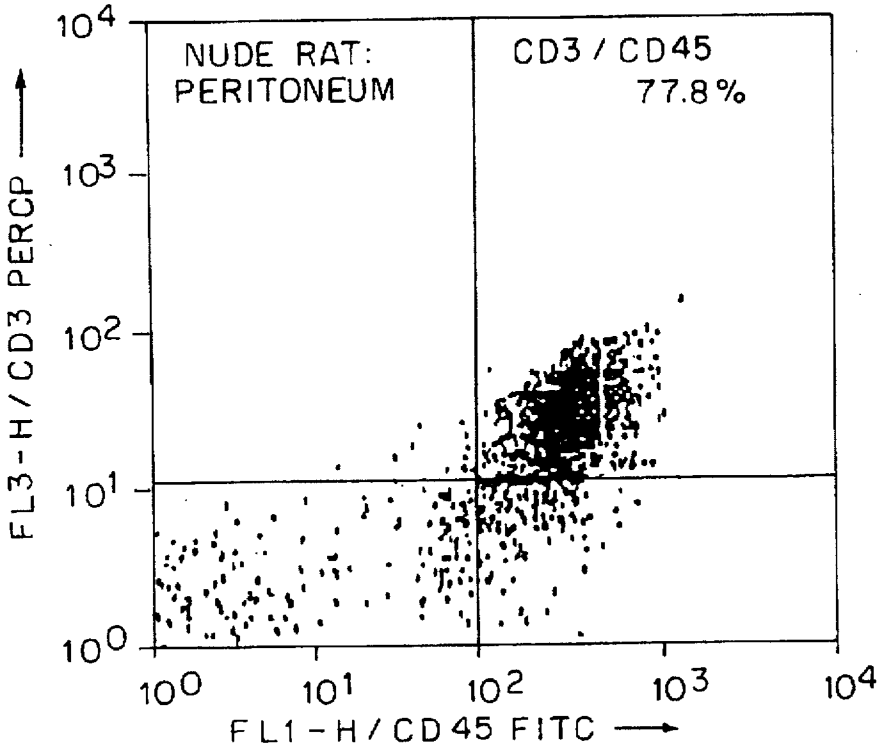
FIGS. 9A–9B are a representation showing an engraftment of human T lymphocytes in the peritoneum of nude rats, 17 days following transplantation of $300\times10^6$ human PBL i.p., as shown by double staining with CD3/CD45 (FIG. 9A) and CD4/CD8 (FIG. 9B).
Figure 9B:
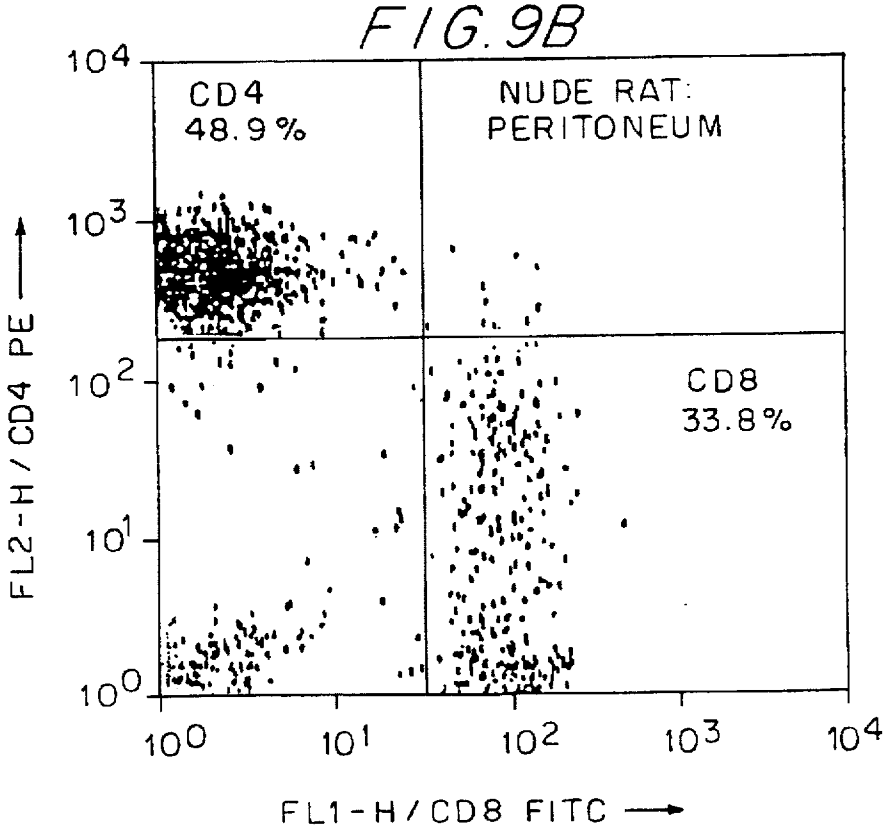

Engraftment of human PBL was also shown to be successful in nude rats following split TBI of 4 Gy+10 Gy at an interval of 3 days (FIGS. 9A–9B).

TABLE II

Engraftment of human T lymphocytes and Ig production in normal BALB/c mice following lethal single dose and split dose TBI

| | 10 Gy TBI | 4 + 10 Gy TBI |
|---|---|---|
| $CD3^+/CD45^+$ (%) | 7.3 ± 10.5 | 33.5 ± 25.1 |
| n | 11 | 25 |
| Hu—Ig (μg/ml) | 0 | 220 ± 222 |
| n | 12 | 15 |

TABLE III

Engraftment of human T lymphocytes and Ig production in BNX mice following non-lethal and lethal TBI

| | 4 Gy TBI | 12 Gy TBI |
|---|---|---|
| $CD3^+/CD45^+$ (%) | 8.5 ± 12 | 54 ± 19 |
| Hu—Ig (μg/ml) | 7 ± 13 | 67 ± 25 |
| n | 7 | 8 |

EXAMPLE X

Engraftment of Human Colon Cells into Lethally Irradiated BNX Mice

Figure 10:
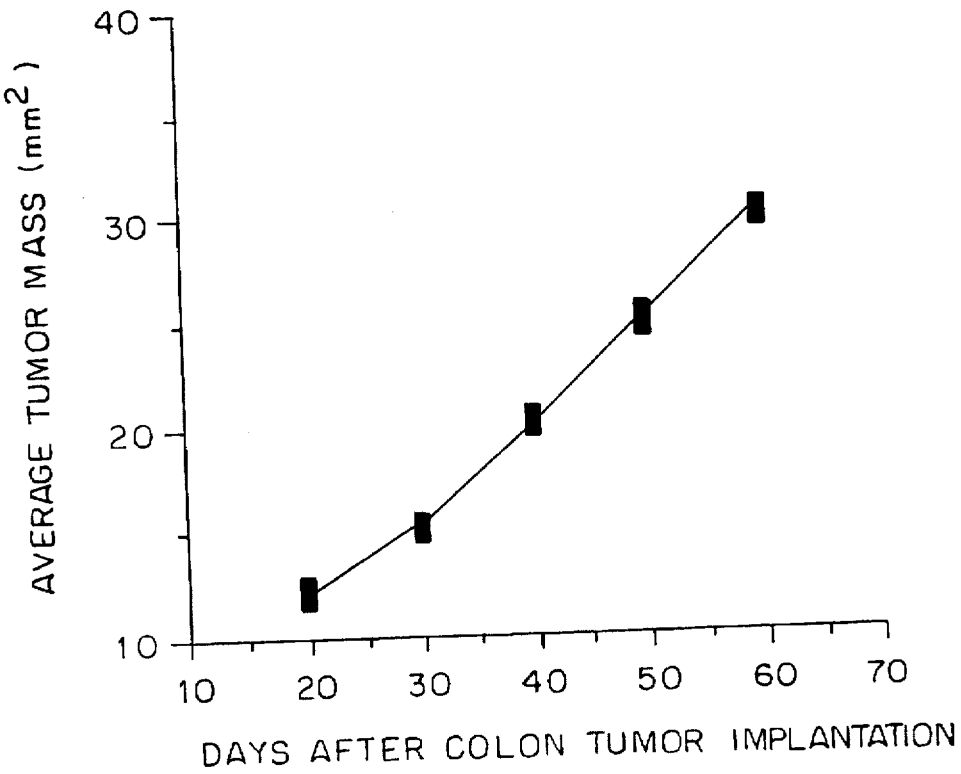
FIG. 10 is a representation showing the average tumor size as a function of time after subcutaneous implantation of colon carcinoma cells.

Eight to twelve-week old female BNX mice (obtained from Harlan Sprague Dawley, Indianapolis) were exposed to a single dose of 12 GyTBI from a Gamma beam 150-A $^{60}$Co source with a focal skin distance (F.S.D.) of 75 cm, at a dose rate of 0.7– 0.9 Gy/min. One day later, 2×10$^6$ colon cells from an established tumor cell line (J. Fogh and G. Trempe, in *Human Tumor Cells in Vitro* (1975), E. Fogh (ed.), New York, Plenum, pp. 115–159) were transplanted subcutaneously into each mouse. Twenty-four hours later, T cell-depleted bone marrow cells (2×10$^6$) from 8 to 12 week-old male SCID mice (obtained from the Weizmann Institute Animal Breeding Center), prepared according to Reisner et al. (1978) *Proc. Nat'l Acad. Sci. USA* 75:2933, with minor modifications according (Schwartz (1987) *J. immunol.* 138:460, were transplanted into treated mice by intravenous insfusion on the second day post TBI. Tumor growth was followed and the results presented in FIG. 10.

EXAMPLE XI

Engraftment of Human Hepatitis C Virus (HCV)-Infected Liver Tissue into BNX Mice BNX mice (12) were lethally irradiated as in Example X and transplanted with T-cell depleted SCID mice bone marrow and small pieces of liver tissue of a hepatitis C patient were grafted under the kidney capsules. After 1 or 2 weeks, the mice were tested by PCR for HCV antigen (5'-non-coding region). None of the animals was positive after 1 week, but after 2 weeks 6 of the 12 mice infected were HCV positive.

EXAMPLE XII

Transplantation of Organs

BALB/c or BNX chimeric mice were obtained according to Examples VII and VIII above. Small pieces (approximately 1 cm$^2$) of human tissue: thymus, liver, spleen, and lymph node were grafted under the kidney capsules of the BALB/c or BNX chimeric mice, as described by Nakamura et al., cited above, two weeks after TBI irradiation of the BALB/c or BE mice (Day 0) followed by transplantation of SCID bone marrow ($1\times10^6$ cells) (Day 1). Takes of grafted human tissue are evaluated by histology and/or by immunohistochemistry. Immunohistological tests of thymus implants suggest that, within an observation period of one month after transplantation, the stroma structure of human thymus implants was accepted and maintained under the kidney capsules of the BALB/c or BNX mice.

Vascularised human liver (not shown) has lost its typical architecture, but human hepatocytes and other components, such as bile ducts and Kupfer cells, could be identified by histological examination.

EXAMPLE XIII

Lack of GVHD in Chimeric Mice According to the Present Invention Without Use of Immunosuppressive Agents.

Figure 11:
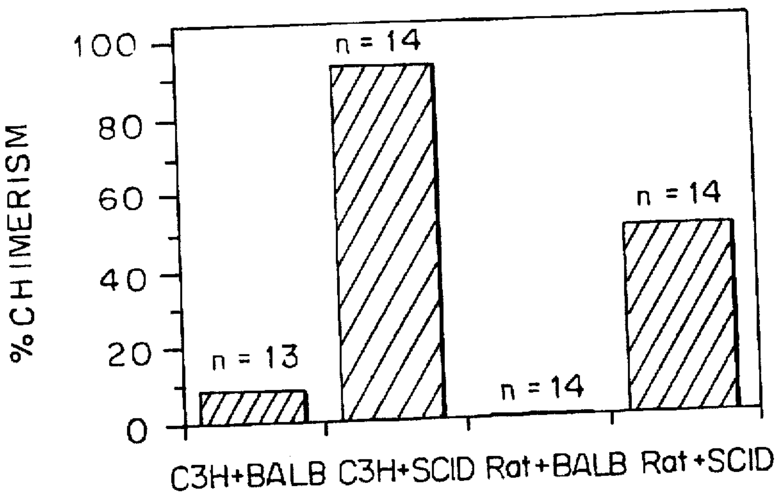
FIG. 11 is a representation showing the long term allogeneic (C3H+BALB and C3H+SCID) and xenogeneic (Rat+BALB and Rat+SCID) donor type chimerism in peripheral blood T cells of BALB recipient mice, assayed by double staining (with anti-Thy1.2 and anti-H-$2^k$ or rat anti-CD4 and anti-rat class I, respectively), 2–3 months post-BMT. T cell depleted C3H (H-$2^k$) bone marrow ($2\times10^6$ cells) or rat bone marrow ($20\times10^6$ cells) were transplanted together with $1\times10^6$ T cell depleted bone marrow cells from BALB/c donors (as in the Sachs' model) or with $1\times10^6$ cells from SCID bone marrow (as in the model of the present invention).

In a model according to the present invention, administration of IL-2 is not needed or used in order to avoid GVHD (graft-versus-host disease) completely. In contrast to the autologous bone marrow in Sachs' model, the SCID bone marrow which is used for radioprotection cannot produce T or B lymphocytes, due to its inherent deficiency. Thus, the present invention avoids the problem of host-versus-graft reaction not by active specific tolerance induction but rather by inducing a permanent state of hematopoietic deficiency. By the method of the present invention, a marked lymphoid chimerism following transplantation of T cell depleted allogeneic bone marrow or human bone marrow together with the SCID bone marrow. To illustrate this difference, in lethally irradiated BALB/c mice, the chimerism obtained after transplantation of T cell depleted C3H (H-$2^k$) bone marrow plus T cell depleted SCID (H-$2^d$) bone marrow to T cell depleted C3H bone marrow plus T cell depleted autologous bone marrow (BALB/c) (H-$2^d$). As can be seen in FIG. 11, when the allogeneic bone marrow depleted of T cells are transplanted with SCID bone marrow, a marked lymphoid engraftment of the allogeneic cells is found without GVHD, whereas if the Sachs' approach is tested and we transplant T cell depleted autologous bone marrow (instead of the SCID bone marrow) together with the same T cell depleted allogeneic bone marrow, the latter cells do not engraft. Moreover, as shown below, the SCID bone marrow can be taken from an H-2 mismatched donor, as opposed to the Sachs' model, which necessitates the use of autologous bone marrow. Thus, the two models are based on fundamentally different principles and lead to entirely distinct mice.

It has been shown that several mouse and human cytokines are not cross reactive between the species, at least not with the same efficiency. Therefore, any extrapolation from an allogeneic transplantation mouse model or even from a rat to mouse transplantation model, to the transplantation of human bone marrow in mice is not obvious. Moreover, primary antibody responses are extremely inefficient in allogeneic mouse models of bone marrow transplantation. The achievement of the present invention in obtaining primary human anti-DNP response in some human/mouse chimera could not be considered obvious on the basis of our relevant murine model and clearly not by the irrelevant Sachs' model. Even if the Sachs' model was based on a similar principle to our model, the engraftment of human cells in lethally irradiated mice and their ability to induce human antibodies against DNP-KLH could not be anticipated by extrapolation from any existing murine model.

EXAMPLE XIV

Lack of Need for M2 H-2 Compatible Hematopoietic Cells With Mammal M1

(i) Studies in the allogeneic murine model verified that the recipient strains need not be BALB/c and we were able to achieve long-term engraftment of T cell depleted BALB/c bone marrow in lethally irradiated C3H recipients when the transplant was administered together with bone marrow from CB17 SCID (H-$2^d$) mouse.

(ii) SCID bone marrow (H-$2^d$) need not be H-2 compatible with the recipient mouse. Thus, transplantation of human PBL into lethally irradiated C57BL/6 nude mice (H-$2^b$) was engrafted when administered one day after transplantation of T cell depleted SCID bone marrow (H-$2^d$). Likewise, lethally irradiated BNX mice (outbred) transplanted with SCID bone marrow were engrafted successfully with human PBL (as documented by double staining of the chimeric PBL or spleen cells with anti-Leu4 and anti-CD45).

(iii) Moreover, as shown in Example IX, even rats could be engrafted simultaneously with mouse SCID bone marrow (which generated red blood cells) and with human PBL.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A method for evaluating the efficacy of a therapeutic agent or modality potentially useful for treating a human disease, comprising:

(a) providing a chimeric mouse or rat M4 having xenogeneic cells or xenogeneic tissue, said mouse or rat M4 comprising a mouse or rat M1, other than a SCID mouse the hematopoietic cells of which have been substantially destroyed, said mouse or rat M1 having transplanted therein cells or tissue from at least two different sources, at least one of said sources being hematopoietic cells from a mouse M2 having a T and/or B cell immunodeficiency, and at least a second of said sources being human cells or tissue which are either (i) pathological or diseased cells or tissue, or (ii) normal cells or tissue susceptible to being infected by a pathogen causing the human disease, wherein said T and/or B cell immunodeficiency of said mouse M2 is such that the T and/or B cell immunodeficiency can be reconstituted with xenogeneic hematopoietic cells, (b) when said cells or tissue are said normal cells or tissue, infecting said mouse or rat M4 with a pathogen;

(c) treating said mouse or rat M4 with the therapeutic agent or modality; and (d) testing said mouse or rat M4 for signs of said disease or for symptoms associated with said disease, the efficacy of said agent or modality being inversely related to the extent of said signs or symptoms.

2. A method according to claim 1 wherein said disease is AIDS and said pathogen is an HIV.

3. A method according to claim 1, wherein said disease is hepatitis and said pathogen is a human hepatitis virus.

4. A method according to claim 3, wherein said hepatitis virus is a hepatitis C virus.

5. A method according to claim 1, wherein said pathogen is a virus or toxin.

6. A method in accordance with claim 1, wherein said chimeric mouse or rat M4 is one in which said human cells or tissue are normal human cells or tissue susceptible to being infected by a pathogen causing the human disease.

7. A method according to claim 6, wherein said disease is AIDS and said pathogen is an HIV.

8. A method according to claim 6, wherein said pathological human cells are hepatitis C virus infected cells.

9. A method according to claim 6, wherein said pathogen is a virus or toxin.

10. A method in accordance with claim 1, wherein said chimeric mouse or rat M4 is one in which said human cells or tissue are pathological or diseased cells or tissue.

11. A method according to claim 10, wherein said pathological or diseased cells or tissue is selected from the group consisting of an autoimmune cell, a cancer cell, a pathological blood cell, a human T cell, a lymphokine-activated killer cell, a cytotoxic T lymphocyte, a human T cell derived cell and a human B cell derived cell.

12. A method according to claim 1, wherein said chimeric mouse or rat M4 is one in which said human cells or tissue are pathological cells or tissue.

13. A method according to claim 12, wherein said pathological human cells or tissue are malignant cells or tissue selected from the group consisting of solid tumor cells or tissue and leukemia cells or tissue.

14. A method according to claim 12, wherein said mammal M1 is a mouse, said mammal M2 is a mouse, and said pathological human cells or tissue are cells or tissue of cancer samples selected from the group consisting of colon cancer, breast cancer, ovary cancer, pancreas cancer, lung cancer, stomach cancer, kidney cancer, prostate cancer, melanoma, neuroblastoma, glioblastoma, myeloid leukemia, lymphatic leukemia, and monocytic leukemia.

15. A method according to claim 14, wherein said human pathological cells or tissue are melanoma cells or melanoma tissue.

16. A method in accordance with claim 12 for chemotherapy sensitivity testing of a drug against a human solid tumor, wherein said chimeric mouse or rat M4 is one in which said pathological human cells or tissue are human solid tumor cells or tissue and said testing step comprises evaluating the effect of said chemotherapy on said solid tumor cells or tissue.

17. A method according to claim 16, for testing the chemotherapy activity of a drug against the tumor tissue of an individual patient, wherein said chimeric mouse or rat M4 is one in which said human solid tumor cells or tissue originate from the tumor of said individual.

18. A method in accordance with claim 12 for chemotherapy sensitivity testing of a drug against leukemia, wherein said chimeric mouse or rat M4 is one in which said pathological human cells or tissue are human leukemia cells and said testing step comprises evaluating the effect of said chemotherapy on said leukemia cells.

19. A method according to claim 18 for testing the chemotherapy activity of a drug against the leukemia cells of an individual patient, wherein said chimeric mouse or rat M4 is one in which said human leukemia cells originate from leukemia cells of said individual.

20. A method in accordance with claim 12, wherein said chimeric mouse or rat M4 is one in which said human cells or tissue are malignant cells or tissue.

21. A method according to claim 20, wherein said malignant cells or tissue are obtained by a biopsy from a human cancer patient.

22. A method in accordance with claim 20, wherein said testing step comprises evaluating the effect of said therapeutic agent or modality on said malignant cells or tissue.

23. A method in accordance with claim 1, wherein said testing step comprises testing for the presence or amount of said pathogen or of an antigen of said pathogen in a body fluid or tissue of the treated chimeric mouse or rat M4.

* * * * *